(12) United States Patent
Röttger et al.

(10) Patent No.: US 9,408,942 B2
(45) Date of Patent: Aug. 9, 2016

(54) FLEXIBLE, STRONGLY ABSORBING MATERIAL

(75) Inventors: Henning Röttger, Kaltenkirchen (DE); Stefanie Lutter, Wittstock (DE); Ralf Ehmke, Meyenburg (DE)

(73) Assignee: GLATFELTER FALKENHAGEN GMBH, Pritzwalk (DE)

( * ) Notice: Subject to any disclaimer, the term of this patent is extended or adjusted under 35 U.S.C. 154(b) by 467 days.

(21) Appl. No.: 13/575,725

(22) PCT Filed: Jan. 28, 2011

(86) PCT No.: PCT/EP2011/000391
§ 371 (c)(1),
(2), (4) Date: Jul. 27, 2012

(87) PCT Pub. No.: WO2011/092025
PCT Pub. Date: Aug. 4, 2011

(65) Prior Publication Data
US 2012/0302983 A1    Nov. 29, 2012

(30) Foreign Application Priority Data

Jan. 28, 2010 (DE) .......................... 10 2010 006 228

(51) Int. Cl.
*A61F 13/15* (2006.01)
*A61L 15/60* (2006.01)
(Continued)

(52) U.S. Cl.
CPC ........... *A61L 15/60* (2013.01); *A61F 13/15658* (2013.01); *A61F 13/534* (2013.01);
(Continued)

(58) Field of Classification Search
CPC . A61F 13/539; A61F 13/537; A61F 13/5116; A61F 13/53; A61F 13/15764; A61F 13/15707; A61F 13/15747; A61F 2013/15878; A61F 2013/15821; A61F 2013/530481; A61F 2013/530131
USPC ......... 604/378, 367, 368, 370, 372, 374, 375, 604/377, 385.101; 162/12, 157.2, 158; 156/265, 62.2, 305
See application file for complete search history.

(56) References Cited

U.S. PATENT DOCUMENTS

| | | | |
|---|---|---|---|
| 5,378,528 A | 1/1995 | Makoui | |
| 5,607,414 A * | 3/1997 | Richards et al. | ............... 604/378 |

(Continued)

FOREIGN PATENT DOCUMENTS

| | | |
|---|---|---|
| DE | 199 18 343 | 10/2000 |
| DE | 102 32 078 | 3/2004 |

(Continued)

*Primary Examiner* — Jacqueline Stephens
(74) *Attorney, Agent, or Firm* — Blank Rome LLP

(57) ABSTRACT

The invention relates to an absorbent structure having a sequence of layers, comprising at least one first and one second outer layer and at least one liquid storage layer arranged therebetween, wherein the layers are arranged on top of each other and form a layer structure, wherein at least the liquid storage layer comprises a cellulose material, preferably cellulose fibers, and a super-absorbent polymer SAP, preferably SAP particles and/or SAP fibers, wherein the liquid storage layer comprises at least less, preferably no, binder than liquid-storing layers of the absorbent structure adjacent to the liquid storage layer. The absorbent structure has particularly high flexibility in the wet and the dry state. It can preferably be used in disposable items. The invention further relates to a method for producing the absorbent structure and to a device for producing same.

19 Claims, 9 Drawing Sheets

(51) Int. Cl.
*A61F 13/534* (2006.01)
*A61L 15/28* (2006.01)
*B32B 5/26* (2006.01)
*B32B 33/00* (2006.01)
*A61F 13/539* (2006.01)
*A61F 13/511* (2006.01)
*A61F 13/537* (2006.01)
*A61F 13/53* (2006.01)

(52) U.S. Cl.
CPC ........... *A61F13/53743* (2013.01); *A61L 15/28* (2013.01); *B32B 5/26* (2013.01); *B32B 33/00* (2013.01); *A61F 13/15707* (2013.01); *A61F 13/15747* (2013.01); *A61F 13/15764* (2013.01); *A61F 13/5116* (2013.01); *A61F 13/537* (2013.01); *A61F 13/539* (2013.01); *A61F 2013/15821* (2013.01); *A61F 2013/15878* (2013.01); *A61F 2013/530131* (2013.01); *A61F 2013/530481* (2013.01); *B32B 2250/20* (2013.01); *B32B 2255/02* (2013.01); *B32B 2255/26* (2013.01); *B32B 2262/02* (2013.01); *B32B 2262/062* (2013.01); *B32B 2262/12* (2013.01); *B32B 2262/14* (2013.01); *B32B 2264/02* (2013.01); *B32B 2307/726* (2013.01); *B32B 2555/02* (2013.01); *Y10T 442/668* (2015.04)

(56) References Cited

U.S. PATENT DOCUMENTS

| | | |
|---|---|---|
| 5,821,179 A | 10/1998 | Masaki et al. |
| 6,562,742 B2 | 5/2003 | Dutkiewicz et al. |
| 2002/0165509 A1 | 11/2002 | Baer et al. |
| 2004/0122394 A1 | 6/2004 | Fell et al. |
| 2006/0184149 A1 | 8/2006 | Kasai et al. |
| 2010/0030177 A1 | 2/2010 | Sanada et al. |

FOREIGN PATENT DOCUMENTS

| | | |
|---|---|---|
| DE | 102 51 137 | 5/2004 |
| DE | 698 21 794 | 12/2004 |
| DE | 103 27 026 | 1/2005 |
| DE | 10 2004 005 417 | 8/2005 |
| DE | 10 2004 009 556 | 9/2005 |
| DE | 10 2004 015 686 | 10/2005 |
| DE | 10 2004 021 453 | 11/2005 |
| DE | 10 2004 056 154 | 5/2006 |
| DE | 10 2004 024 551 | 12/2012 |
| EP | 1 721 036 | 11/2006 |
| EP | 2 140 844 | 1/2010 |
| WO | 03/034963 | 5/2003 |
| WO | 2005/080655 | 9/2005 |
| WO | 2008/093660 | 8/2008 |

* cited by examiner

| Number | Sample | Fmax N | Extension % | Distance mm |
|---|---|---|---|---|
| 1 | VH600.101 tr. with tape 4024 Tesa | 6.82 | 4.58 | 9.19 |
| 2 | VH600.101 n. with tape, airl., sprayed | 5.06 | 1.92 | 3.86 |
| 3 | VH600.101 n. with tape, airl., sprayed | 5.65 | 2.52 | 5.06 |
| 4 | MT410.104 tr. with tape 4024 Tesa | 34.94 | 5.60 | 11.22 |
| 5 | MT410.104 n. with tape, airl., sprayed | 17.72 | 3.75 | 7.52 |
| 6 | VE500.200 tr. with Tape 4024 Tesa | 41.26 | 2.98 | 5.97 |
| 7 | VE500.200 n. with Tape / airlaid sprayed | 5.59 | 0.96 | 1.92 |
| 8 | VH460.103 tr. with tape 4024 Tesa | 11.66 | 3.80 | 7.62 |
| 9 | VH460.103 n. with tape / airlaid sprayed | 5.65 | 2.35 | 4.72 |
| 10 | VH460.103 with tape / airlaid sprayed | 16.22 | 3.97 | 7.96 |
| 11 | VH460.103 with tape / airlaid sprayed | 16.11 | 3.81 | 7.66 |
| 12 | VH460.103 with tape / airlaid sprayed | 14.75 | 3.84 | 7.70 |
| 13 | VH460.103 with T. + sprayed / 1 min wet | 5.16 | 3.55 | 7.14 |
| 14 | VH460.103 with T. + sprayed / 1 min wet | 4.18 | 3.16 | 6.34 |
| 15 | VH460.103 with T. + sprayed / 1 min wet | 4.92 | 2.72 | 5.46 |
| 16 | VH460.103 with T. + sprayed / 10 min wet | 3.12 | 3.35 | 6.83 |
| 17 | VH460.103 with T. + sprayed / 10 min wet | 3.87 | 4.48 | 9.03 |
| 18 | VH460.103 with T. + sprayed / 10 min wet | 3.26 | 3.78 | 7.64 |
| 19 | VH600.101 with T. + sprayed | 5.13 | 3.58 | 7.19 |
| 20 | VH600.101 with T. + sprayed | 4.04 | 2.88 | 5.81 |
| 21 | VH600.101 with T. + sprayed | 4.94 | 2.62 | 5.26 |
| 22 | VH600.101 with T. + sprayed / 1 min wet | 3.75 | 2.81 | 5.68 |
| 23 | VH600.101 with T. + sprayed / 1 min wet | 3.19 | 2.12 | 4.28 |
| 24 | VH600.101 with T. + sprayed / 1 min wet | 4.21 | 3.21 | 6.48 |
| 25 | VH600.101 with T. + sprayed / 1 min wet | 3.53 | 3.32 | 6.66 |
| 26 | VH600.101 with T. + sprayed / 10 min wet | 2.84 | 3.23 | 6.49 |
| 27 | VH600.101 with T. + sprayed / 10 min wet | 2.99 | 3.98 | 7.99 |
| 28 | MT410.104 with T. + sprayed | 30.09 | 4.83 | 9.73 |
| 29 | MT410.104 with T. + sprayed | 32.03 | 6.46 | 12.93 |
| 30 | MT410.104 with T. + sprayed | 35.17 | 5.51 | 11.03 |
| 31 | MT410.104 with T. + sprayed / 1 min. wet | 19.40 | 3.29 | 6.59 |
| 32 | MT410.104 with T. + sprayed / 1 min. wet | 16.76 | 3.42 | 6.86 |
| 33 | MT410.104 with T. + sprayed / 1 min. wet | 19.22 | 3.69 | 7.41 |
| 34 | MT410.104 with T. + sprayed / 10 min. wet | 16.52 | 5.07 | 10.19 |
| 35 | MT410.104 with T. + sprayed / 10 min. wet | 17.69 | 3.98 | 7.98 |
| 36 | MT410.104 with T. + sprayed / 10 min. wet | 17.18 | 4.42 | 8.88 |
| 37 | VE500.200 with T. + sprayed/ | 50.73 | 6.07 | 12.18 |
| 38 | VE500.200 with T. + sprayed/ | 55.81 | 6.77 | 13.56 |
| 39 | VE500.200 with T. + sprayed/ | 54.23 | 7.54 | 15.11 |
| 40 | VE500.200 with T. + sprayed / 1 min wet | 2.40 | 1.06 | 2.13 |
| 41 | VE500.200 with T. + sprayed / 1 min wet | 2.48 | 1.03 | 2.06 |
| 42 | VE500.200 with T. + sprayed / 1 min wet | 1.55 | 0.79 | 1.58 |
| 43 | VE500.200 with T. + sprayed / 10 min wet | 1.07 | 1.32 | 2.65 |
| 44 | VE500.200 with T. + sprayed / 10 min wet | 1.26 | 2.16 | 4.33 |
| 45 | VE500.200 with T. + sprayed / 10 min wet | 0.72 | 2.57 | 5.23 |

TABLE 5: Tension test for determining shear strength values

FIG. 8

FLEXIBLE, STRONGLY ABSORBING MATERIAL

CROSS REFERENCE TO RELATED APPLICATIONS

This application is the U.S. National Stage of International Application Number PCT/EP2011/000391 filed on Jan. 28, 2011 and claims priority to German patent application 10 2010 006 228.6 filed on Jan. 28, 2010 and U.S. patent application Ser. No. 12/657,982 filed on Jan. 28, 2010, said priority application hereby incorporated by reference.

BACKGROUND OF THE INVENTION

1. Technical Field

The invention relates to a multilayer absorbing structure including at least one liquid storage layer, preferably with a liquid reception layer, a liquid storage layer and a liquid distribution layer using cellulose fibers and a super absorbing polymer. The invention also relates to a method and an apparatus for producing the structure.

2. Description of the Background Art

Multilayer absorbing structures using cellulose and super absorbing polymers abbreviated as SAP, e.g. in the form of SAP particles or SAP fibers have been known for many years and are being used as a layer material in disposable products, e.g. in hygiene products, medical products and industrial products.

Fiber layers with absorbent layer in which binder materials are being used for stabilizing the absorbent layer and for avoiding abrasion of the fibers are known. The layers of such layer material include binder materials, e.g. in the form of fibers, powder, hot melt glues, solvent-binder mixes for application in liquid form or similar.

For example EP 1721 036 describes producing a fiber web made of cellulose fibers with absorbing properties through an airlaid method. The fiber web includes several layers. An inner absorbent layer includes a point bonded cellulose material with a super absorber. In order to prevent creating dust from the fibers, called "linting", which is generated through abrasion or fussing of cellulose fibers, the fibers, in particular in the outer portions of the center fiber web are impregnated with water-latex mix.

When an absorbing structure which includes e.g. a liquid reception layer, a liquid storage layer and a liquid distribution layer is wetted, e.g. by a liquid, the liquid moves from the liquid reception layer to the liquid storage layer through capillary effects. Superfluous liquid can enter from the liquid storage layer into the liquid distribution layer and can be distributed by the liquid distribution layer through pore structure selected accordingly and can be fed back into the storage layer if necessary. This prevents undesirable back wetting effects which can occur through a run out of liquid from a liquid reception layer into a liquid distribution layer and beyond, e.g. onto the skin of a bearer of a hygiene product. However, such products tend to have considerable deficiencies with respect to wearing comfort. Thus, e.g. a liquid storage layer wetted and compressed through liquid absorption and subsequent deformation, this means through regular use, does not tend to go back into its original position after it is unloaded. For example, when SAP particles are loaded with moisture and deformed, a gluing effect between the particles can be created. For known relatively compact liquid storage layers thus the capacity for absorbing additional liquid is substantially reduced which impairs wearing comfort.

SUMMARY OF THE INVENTION

Thus it is desirable to have a product available which helps to avoid such impairments of wearing comfort during use.

Thus, it is the object of the present invention to provide a product, a method and an apparatus for producing an absorbing product which facilitates better properties during use, in particular increased flexibility.

This object is accomplished through an absorbing structure, a method for producing an absorbing structure and an apparatus according to the independent claims. Preferred embodiments are defined in the dependent claims. The features included therein, however, can also be combined in further embodiments with other features from the subsequent description and they are not limited to the embodiments respectively claimed. The respective proposed features, in particular also of the respective independent claims only serve as a first proposal for a solution, wherein one or plural of the features included in the independent claims can also be supplemented and/or replaced by the subsequent features.

Thus, an absorbing structure with a sequence of layers is proposed which includes at least a first and a second outer layer and at least one liquid storage layer disposed there between, wherein the layers are disposed on top of one another and form a ply structure wherein at least the liquid storage layer includes a cellulose material preferably cellulose fibers and a super absorbing polymer SAP, preferably SAP particles and/or SAP fibers, wherein the liquid storage layer includes at least less binder material than liquid storage plies of the absorbing structure adjacent to the liquid storage layer, preferably the liquid storage layer includes no binder material. The adjacent liquid storage plies according to one embodiment can at least include one of the plies, which form the first and the second outer layer of the absorbing structure.

In a preferred embodiment the absorbing structure includes at least one liquid reception layer, at least one subsequent liquid storage layer and at least one subsequent liquid distribution layer, wherein the layers are connected and form a ply structure. The liquid reception layer and/or the liquid storage layer include a cellulose material, preferably cellulose fibers and a super absorbing polymer SAP, preferably SAP particles and/or SAP fibers. The liquid reception layer and/or the liquid distribution layer include a binder material. Contrary to the cellulose fibers of the liquid reception layer and of the liquid distribution layer, the cellulose fibers of the liquid storage layer according to a preferred embodiment are not impregnated with a binder material, or they do not include binder material. Another embodiment provides that a binder material is provided in a low concentration, this means only with a low adhesion within the liquid storage layer. This concentration is e.g. adjusted, so that the adhering connections in the liquid storage layer immediately tear open when a force is introduced, e.g. a shear force and/or when a force is introduced through swelling of SAP, wherein the tearing open of the adhering connections facilitate a degree of freedom of movement. Such a concentration of binder material can e.g. be used to fixate a local disposition of SAP in the liquid storage ply for producing the absorbing structure at least at one point in time. However, when liquid is absorbed the adhering connections can disengage and facilitate movability within the liquid storage ply. For example a usable binder material can lose its bond when wetted by a liquid. A shear force can also occur when an absorbing structure is being used, which shear force then disengages the adhering connection and establishes the movability in the liquid storage ply.

Preferably, the ply structure according to an embodiment includes at least the following assembly:
- a first ply, comprising at least a treated fluff pulp, multi component fibers, preferably PE/PET-bi component fibers and a super absorber;
- a second ply, comprising at least a treated and/or non treated fluff pulp and a super absorber; and
- a third layer, comprising at least a non treated fluff pulp and multi component fibers, preferably PE/PET bi component fibers.

In order to support the first ply, its outer surface can additionally be provided with a paper-tissue ply. In one embodiment this ply structure comprises a loose compression through a calendering step, preferably through a smooth roller calender, whereby a first thickness, e.g. a final thickness of the ply material can be adjusted.

Furthermore, a latex binder, e.g. an EVA-dispersion binder can be applied to one or both outer surfaces of the layer structure, wherein the binder is subsequently dried and hardened. Contrary to conventional materials, the suggested configuration of the ply structure facilitates that the super absorber can expand freely in the center layer after liquid is introduced, which center layer is preferably formed by the liquid storage layer or at least co-formed by the liquid storage layer, since the super absorber is not impeded by the bonding fibers. This expansion process is e.g. not impeded by a pulp-bico-ply which is stiffened by an EVA dispersion binder, but otherwise open.

Preferably this provides an elastic ply structure which comprises solid outer layers and at least one loose, hardly compacted inner ply.

The ply structure can also be produced without a tissue ply and/or with other support plies, e.g. spunbond layers or fleeces produced in any manner.

The ply material according to one embodiment has a substantially constant thickness which is in an order of magnitude of approximately $0.1$ $g/cm^3$. It can also be in a range of $0.08$ to $0.15$ $g/cm^3$. According to another embodiment, the layer material in dry state at a thickness of approximately 5 mm can have a surface weight of approximately 460 $g/cm^2$ and for a thickness of approximately 6 mm it can have a surface weight of approximately 600 $g/cm^2$. A surface weight in a range between 440 $g/cm^2$ and up to 600 $g/cm^2$ is desirable. A thickness between 4.7 mm and 6.7 mm of the absorbing structure is also desirable. This is a manufactured layer thickness of the ply structure which the ply structure can have in a dry state. Besides these preferred layer thicknesses, layer thicknesses between 3 mm and 15 mm, preferably between 4 mm and 8 mm are conceivable for the ply structure according to the invention as a function of the respective use of the ply structure and the liquid volume associated therewith or as a function of the frequency of the liquid provision within a short time interval. When wetting the ply structure, this means in wet condition, the layer thickness will change much less due to the enormous receiving capability of the liquid receiving layer and due to the relative movability of the adjacent layers, than this is known for conventional products. The increase in layer thickness as a function of the degree of saturation is in a range of 50-150% with reference to the initial thickness of the layer structure.

Surprisingly, it has become evident that the ply material has substantial advantages over the known fluff pulp SAP ply structures or ply structures with homogenously thermally bonded layers, in which all layers are provided with binder materials, e.g. bi component fibers. The proposed layer structure has proven advantageous in used condition, thus in wet condition.

Thus, it has e.g. become evident that the absorbing structure has the advantage that the liquid storage layer during use of the absorbing structure can substantially revert back to its original state in spite of multiple liquid absorptions and pressure loadings. Since no bonding fibers are provided, the super absorbing material is not prevented from free swelling. Thus, e.g. the desired parameter of the free swelling capacity, the so called free swell capacity, which is preferably in the range of 20 g/g, can be achieved with comparatively lower SAP percentages and lower surface weights than this is provided for conventional ply structures. This helps reduce the cost for raw materials. According to an embodiment, the free swelling capacity is in a range between 17 g/g and 24 g/g.

Additionally, it was observed for known ply structures that the super absorber acts like glue after liquid is introduced and fixates the layer in the formed shape. When the loose material is deformed and fixated in this form, it has no more propensity to assume its original shape. Supported by gravity, it forms lumps, the so called sagging which degrades wearing comfort and absorption performance, since the super absorber is not distributed in the liquid layer in an optimum manner any more. The proposed layer structure overcomes these disadvantages, so that a material with reduced wet stiffness, this means greater movability and a high wearing comfort is provided compared to the respective identical material which includes a binder material within the liquid storage layer.

It has furthermore proven advantageous that the SAP material which is already disposed in the liquid reception layer immediately absorbs incoming liquid and thus facilitates a quicker transportation of the liquid from its location of introduction to the core of an absorber product. This helps to avoid back wetting effects, e.g. through run out of excess liquid for a high liquid volume towards the bearer of absorbing product. Furthermore, an improvement of the re-wetting capability of the absorbing structure is facilitated.

An improvement of the invention provides that the absorbing structure includes at least 3 plies, wherein a center ply comprises at least less, preferably no binder material.

It is also provided that all layers of the layer structure respectively comprise at least one air laid material preferably as a main component of the layer, wherein the respective layers themselves can be configured in multiple plies. For example the liquid reception layer, the liquid storage layer and/or the liquid distribution layer can include one or several functional layers besides the air laid layer, which improve the desired effect of each of these layers. Preferably, the particular layers of a ply can be arranged, so that a property gradient can be generated from an outer surface of the ply to another outer surface. On the other hand the layers of a ply can be configured, so that an optimum for the desired property is generated within a ply.

Another embodiment of the invention provides that the center ply is at least made with less binder material, preferably made without binder material, and that it is at least substantially made of treated and/or untreated cellulose material.

According to an embodiment, the binder material of the liquid reception layer and/or of the liquid distribution layer is configured as thermal plastic fibers, preferably multi component fibers, particularly preferably bi component fibers.

According to another embodiment of the invention SAP particles and/or SAP fibers are disposed moveable relative to one another in the liquid storage layer when liquid is absorbed and/or under pressure.

In an embodiment of the invention the ply structure has a first and a second surface, wherein the first and/or the second surface respectively comprises a binder material layer which is preferably latex based.

According to a preferred embodiment the absorbing structure comprises a paper tissue layer, a second layer with fluff pulp, bonding fibers and super absorber, a third layer with fluff pulp with at least less bonding fibers than the respective second layer and the respective fourth layer, preferably without bonding fibers and with super absorber and a fourth layer with fluff pulp and bonding fibers.

According to the embodiment of the invention the liquid reception layer includes a large volume fleece made of treated and/or untreated cellulose material.

Particular plies of the absorbing structure can include:
respectively the same type of cellulose fibers;
respectively different types of cellulose fibers;
mixtures thereof;
chemically or physically treated cellulose fibers;
non treated cellulose fibers;
mixtures of treated and non treated cellulose fibers;
synthetic fibers by themselves or mixed with cellulose fibers in treated or non treated form; and
mineral fibers by themselves or mixed with synthetic and/or cellulose fibers.

Particular layers can also exclusively include cellulose fibers.

The term "cellulose fibers" in the context of this disclosure is not interpreted in a restrictive manner. All natural fibers can be used which are capable or made capable through chemical or physical treatment to receive liquids and preferably also to bind liquids. Synthetic fibers and mineral fibers can also be processed through the same treatment.

As a matter of principle all layers of the ply structure can include treated and/or non treated cellulose fibers. However, it has proven useful that the liquid reception layer includes an air laid layer which includes essentially chemically and/or physically non treated cellulose fibers. According to another embodiment the cellulose fibers of the liquid distribution layer are not chemically and/or physically treated.

Chemical treatments are e.g. the following:
washing processes, extraction processes;
bleaching processes;
dying processes;
fibrillation processes using solvents;
surface treatment preferably for hydrophilization, increase of strength or elasticity, e.g. through spraying, dipping, drenching, washing
and similar.

A physical treatment can be performed through:
comminution and fibrillation, e.g. cutting, milling, defibration,
classification, e.g. air classification.

Depending on the decomposition process and the bleaching process of the fibers, defined property combinations can be achieved in the cellulose fibers.

For example, preferably untreated fibers are used in the liquid storage layer. This has various reasons. By adding treatment materials, in particular surface treatment materials, the pulp loses absorption capability. In order to assure the best possible absorption in a liquid storage layer, preferably a non-treated pulp type is being used. It can be compressed best in the process, since the non-treated fibers adhere together well.

In the layer structure according to the invention, the following components can be advantageously disposed, respectively with reference to the total weight of the layer structure:

2-10% by weight of a tissue, preferably 3-4% by weight;
20-60% by weight cellulose fibers in treated form or in non-treated form, preferably 35-45% by weight, particularly preferably respectively 15-25% by weight, treated or untreated cellulose,
30-50% by weight superabsorber material, preferably 40-45% by weight,
1-5% by weight of a first binder material, preferably 3-4% by weight, wherein the first binder material preferably comprises a polymer dispersion, a latex binder is particularly preferred,
3-10% by weight of a second binder material, preferably 5-7% by weight, wherein the second binder material includes multi-component fibers, preferably bi-component fibers on the basis of polyethylene and polyethylene terephthalate (PET),
wherein the cited ranges of the components can be distributed in portions over the particular plies of the structure, or one or several components can be omitted in a particular ply.

When the absorbing structure absorbs liquid and/or is exposed to a slight pressure, at least the SAP particles and/or the SAP fibers of the liquid storage layer are capable during liquid absorption and/or under slight pressure to substantially retain their external shape. This loading causes a swelling of the SAP particles and/or the SAP fibers and possibly a deformation. After unloading, the SAP material is configured to substantially revert back to its original shape.

An embodiment of the absorbing structure provides that the absorbing structure includes a paper tissue ply as a first ply, a second ply with fluff pulp, bonding fibers and super absorber, a third ply with fluff pulp and with super absorber, and a fourth layer with fluff pulp and bonding fibers, wherein the third ply includes at least less bonding fibers than the respective second and fourth plies, preferably it is without bonding fibers. According to an embodiment, it is provided that the third ply facilitates relative movability between the second and the fourth ply in a longitudinal direction of the absorbing structure in a wet state of the absorbing structure.

The super absorbing material e.g. provided as SAP particles and/or SAP fibers recited supra is capable of swelling and typically transitions into a gel type condition. Thus, they cannot only store water. Rather, the SAP particles are capable for a disposition in the ply structure as described supra to generate a drawn flow, thus functioning e.g. as a drainage material for the liquid distribution layer.

From a chemical point of view, SAP can be copolymers, which include acrylic acid and sodium acrylate, wherein the ratio of the two monomers relative to one another can vary. Additionally, e.g. crosslinking materials are added for polymerization, which link the formed long chain polymer in particular locations through chemical bridges. The properties of the polymer can be adjusted as a function of the degree of crosslinking. For example, SAP materials can be used as they are shown in EP 08 10 886, in particular also shown in the art cited therein, which is incorporated into the disclosure by reference in its entirety. An embodiment provides e.g. that SAP particles include a coating. The coating can e.g. dissolve when it comes in contact with a liquid, in order to enable the absorption of the liquid through the SAP particle in the first place. Furthermore, SAP material can be used as respectively evident from DE 10 2004 015 686 A1, DE 698 217 94 and/or DE 10 2004 005 417 A1 respectively, in particular with reference to the structure, the geometry of the super absorbing polymer and also the materials and methods employed in its production. These documents are incorporated into the disclosure in an exemplary manner. Another embodiment provides that the SAP particles can be granular, or they can also have a different geometry. They can e.g. be fibrous, round or shaped differently. Fibers with a super absorber content can be derived e.g. from DE 102 32 078 A1 and also DE 102 51 137 A1. These are also incorporated in the instant disclosure by reference.

The respective layers thus can include identical or different types of cellulose fibers and/or SAP particles and/or SAP fibers. This way, the absorption properties of the layer structure for liquids can be adjusted in a defined manner.

For example, highly permeable SAP particles and/or SAP fibers can be used in one ply, which cause a two-stage absorption and storage effect together with SAP particles and/or SAP fibers in another ply. For example, SAP particles and/or SAP fibers with high absorption capability can be provided in a ply that faces the liquid reception layer, and semi-permeable SAP particles and/or SAP fibers can be provided in another ply. This can provide a buffer function in the additional ply, which is advantageous in particular when liquid is introduced several times.

In a preferred embodiment of the invention, the SAP particles and/or SAP fibers remain disposed movable relative to one another in the liquid storage layer for liquid reception and/or slight pressure. This is facilitated by not providing binder material in the liquid storage layer, e.g. in the form of thermoplastic fibers like e.g. multi-component fibers. Thus, the SAP particles and/or SAP fibers can move in the liquid storage layer, expand well, since there is sufficient space for swelling, which improves the absorption properties of the layer structure, and they can simultaneously generate free spaces again, in which a liquid can be stored for another liquid introduction. Thus, such a product can comply with the requirements for incontinence products. Furthermore, the ply can contribute to an improvement of the straining properties of the ply structure, e.g. also with respect to an elastic property. Since the cellulose fibers in the layer structure are not glued together or brought in contact through a binder material, these fibers and/or the SAP material are disposed movable relative to one another. Even in used condition, the so-called wet condition; there is no impairment or only minor impairment of the components of this layer. Furthermore, the SAP material in particular the SAP particles act after swelling, which occurs with a crosslinking or post-linking on the surface of the particles, like a "lubricant", or the liquid storage layer in its entirety acts overall like a "sliding layer" between the liquid reception layer and the liquid distribution layer. Preferably, the SAP particles in dry state already have mostly arc shaped sections at their surfaces, so that preferably spherical particles are created in swelled condition, which only introduces insubstantial changes for the external configuration of the particles, when transitioning from dry state into wet state.

The substantially spherical particles provide movability within the liquid storage layer, and between the liquid storage layer and the particular layers of the layer structure, when using the absorbing structure, wherein the movability yields improved wearing comfort for a disposable product made from the ply structure. The movability of the SAP particles or SAP fibers in the liquid storage layer means that the particles in humidified and swelled condition, this means in wet condition, are still capable to move and slide on one another under load. In unloaded condition, even a partial rolling movement can occur, which has the effect that an inner layer configured as a liquid storage layer can substantially return to its original condition after unloading. In wet state, the outer layers of the layer structure decouple and the SAP enlarged to form a solid gel forms a movable sliding intermediary layer, in which the gel easily facilitates the lateral relative movement in the X-Y surface like a ball bearing. This provides wearing comfort without sacrificing material integrity. The outer layers bonded by a moisture resistant dispersion binder maintain their desired textile properties with reset forces, so that the material overall retains the capability to follow a predetermined shape. Also, when changing shape, the material does not act in a plastic manner like conventional wet layers made of fluff pulp and SAP. The movability of the layer structure and a textile property proximal to the surface are thus maintained.

Thus, e.g. acting compression-, shearing- or tension forces, which can be imparted upon the layer structure from the outside by using an absorber product, can be compensated by the movability of the liquid reception, liquid storage and liquid distribution layer relative to one another, so that a permanent deformation or even a delaminating of the layers during use of the absorber structure is prevented.

Thus, it is not excluded that sporadic components of the binder material of the liquid reception layer and/or of the liquid distribution layer can protrude into the liquid storage layer, and even entirely or partially envelope the cellulose fibers and/or particular SAP particles or fibers. This creates increased strength for the interconnection, wherein in particular the outer surfaces of the liquid storage layer are stabilized in the transition portions towards the respective liquid distribution layer, however, the movability of the layers relative to one another and of the liquid storage layer itself required to obtain good wearing comfort is being maintained.

Thus, e.g. another embodiment for an absorbing structure provides that at least a portion of the binder material, preferably of the bi-component fibers of the liquid distribution layer and/or the liquid reception layer, is mixed with the cellulose material of the liquid storage layer in a transition portion towards the liquid storage layer respectively disposed there between.

In a preferred embodiment of the invention, the binder material includes thermoplastic fibers in the form of bi-component fibers. For example, bi-component fibers in particular core-jacket fibers can be used, in which the jacket has a lower melting point than the core. It is also provided that the bi-component fibers include at least a PET. Preferably, the bi-component fibers include at least a polyethylene, preferably a LDPE or a LLDPE. In a bi-component fiber with a core-jacket structure, a PET or a polymer including polypropylene is provided in the core and a polymer including polyethylene is provided in the jacket. The bi-component fibers are at least softened far enough through heating, so that they form a sticky surface, at which cellulose fibers and also other components of the layer and also components of adjacent layers are attached when a cooling occurs. According to an embodiment, cellulose bonding fibers can be used as they can be derived from DE 69 80 80 61, which is incorporated by reference.

Furthermore, the layers of the liquid distribution layer and/or the liquid storage layer and/or the liquid reception layer can at least partially transition within one another within the respective transition portion.

Thus, it is assured that the layers of the ply interconnection of the absorbing structure have very good cohesion in comparison to conventional products, not only in dry state but also in wet state, while still being movable relative to one another, which facilitates sufficient wet tear resistance, while maintaining good wear comfort. The tear resistance of the ply structure according to the invention in dry state is in a range between 15 to 27 N, and in wet state between 4 to 7 N, wherein the bending stiffness of the ply structure, which determines the wear comfort, only has approximately 3 to 8% of the stiffness in wet condition that it has in dry condition.

Another embodiment of the invention provides that the liquid reception layer and/or the liquid distribution layer are compressed more than the liquid storage layer. The absorbing structure can be configured, so that the liquid distribution layer has a first and a second surface, wherein the first surface is in contact with the liquid storage layer, and wherein the liquid distribution layer is compressed more on its second surface than on its first surface.

The liquid storage layer is preferably configured as a voluminous fleece, and is mostly comprised of cellulose fibers. These can be treated or untreated like in the liquid reception layer or the liquid distribution layer.

Though the particular layers of the ply material are mostly comprised of cellulose fibers, and sporadically comprised of bonding fibers, preferably thermal plastic bonding fibers, it is not excluded that also additional fibers of a natural or synthetic type, e.g. thermoplastic fibers, preferably spunbond fibers, melt blown fibers, staple fibers and similar, are disposed in the layers. Through the selection of the disposition and/or preparation of these fibers, a property gradient can also be generated within a layer of the ply material, or over one or more plies. In order to produce these synthetic fibers, polymers are preferred, which mostly comprise polypropylene, polyethylene, polyester and polyimide.

By using thermoplastic fibers, e.g. in the liquid reception layer, repeated wetting with liquid and transferring this liquid into the liquid storage ply can be improved. For this purpose, the fibers of the liquid reception layer can be configured accordingly and adapted for a particular application, e.g. through hydrophobic configuration, wherein incoming liquid immediately flows in the direction of hydrophilic fibers, or hydrophilic configuration, wherein capillary paths are created in a directed manner, which facilitate a quicker liquid transport.

In an embodiment of the invention, the liquid reception layer, the liquid storage layer and/or the liquid distribution layer include air laid plies or are made of air laid plies.

Furthermore, the absorbing structure can include a support layer, preferably a tissue layer. Thus, the support layer can be disposed at an outside of the liquid distribution layer.

Furthermore, the absorbing layer can include an additional binder layer, e.g. a latex layer, which is disposed on the liquid distribution layer and/or the liquid reception layer.

Accordingly, an embodiment of the invention includes a ply structure with a first and a second surface, wherein the first and/or the second surface include a binder material layer, which is preferably latex based. A non-treated cellulose pulp type is preferably used in the outer liquid reception layer of the absorbing structure in order to generate more volume with longer fibers.

The first and/or the second surface of a layer structure can e.g. be an outer surface of a liquid reception layer or of a liquid distribution layer or of a support layer, preferably of a tissue layer. The absorbing structure can have a gradient with respect to a pore structure which supports an outflow from the liquid reception layer to the liquid distribution layer. The gradient structure can extend within one layer and also over several layers. The gradient can preferably cause an increase of the capillary force. A gradient can e.g. be adjusted through the type of deposition for the cellulose fibers, through additional compression and/or through reduction of the number of pores through additional means, e.g. supplying liquid or binder material, which makes the pores smaller or partially plugs them. This is possible e.g. through latex wetting.

The invention provides a method for producing an absorbing structure, which includes at least the following steps:
  laying fluff pulp, SAP and a binder material as a second ply on a support layer;
  laying fluff pulp and SAP on the second ply as a third ply;
  laying a fourth ply made of fluff pulp and binder on the third ply;
  preferably applying a binder material, preferably a latex based binder material on at least one ply, preferably on the ply structure thus obtained, in particular on an outer ply of the ply structure;
  supplying the ply structure to a calender which includes a calender gap; and
  compression of the ply structure in the calender gap.

The third ply functions according to an embodiment as a receiving ply, the second ply functions as a liquid storage ply and the second ply functions as a liquid distribution ply.

Therefore, preferably the respective plies are made of the listed respective components without an additional component being additionally present in the respective plies, or being fed into the respective plies. Thus, a respective device according to an embodiment only comprises a supply for the respective components, or it is configured according to another embodiment, so that only the components in the respective ply are supplied and other components in the respective ply, which can be supplied in an alternative or supplemental manner, can be blocked and are also blocked.

An embodiment of the invention provides a method for producing an absorbing structure which includes at least the following steps:
  laying at least a first layer, preferably an air laid layer, comprising at least a cellulose material, a binder material, preferably multi-component fibers, for configuring a liquid reception layer;
  laying a ply, preferably an air laid ply, for configuring a liquid storage layer, which comprises at least a cellulose material, preferably cellulose fibers and a super absorbing polymer, preferably SAP particles and/or SAP fibers and no binder material;
  laying a third ply, preferably an air laid ply, for configuring a liquid distribution layer, which comprises at least a cellulose material and a binder material, preferably multi-component fibers;
  preferably applying a binder material layer, preferably latex based, onto a ply, preferably onto the ply structure thus obtained;
  preferably passing the ply structure through a heating device in order to bond the ply structure;
  supplying at least one ply preferably from the ply structure to a calender, comprising at least one smooth roller and an opposite roller forming a calender gap;
  loose compression of the at least one ply preferably of the ply structure in the calender gap.

The invention furthermore provides a device for producing an absorbing structure comprising at least:
  a sifting band for laying plies for forming a ply structure;
  a first forming device through which at least cellulose fibers, SAP and binder materials can be extracted;
  a second forming device through which cellulose fibers and SAP can be extracted, for forming an additional layer;
  a third forming device through which a binder material and cellulose fibers can be extracted as another layer;
  an application station through which a binder material, preferably a latex layer, can be applied at least on an outer surface of the absorbing structure;
  a compression station, preferably a calender, through which the ply structure can be compressed.

An apparatus for producing an absorbing structure, in particular the absorbing structure recited supra, is also proposed, comprising at least:
- a sifting band for laying plies for forming a ply structure;
- a first forming device, through which at least cellulose fibers and a binder material can be applied to the sifting band;
- a second forming device, through which the cellulose fibers and SAP can be applied to the sifting band for forming another ply;
- a third forming device, through which a super absorbing polymer SAP, a binder material and cellulose fibers can be applied as another ply on the sifting band;
- at least one application station, through which a binder material, preferably a latex based binder material, can be applied on the outer surface of the ply structure;
- a compression station, preferably a calender, through which the ply structure can be compressed.

The second forming apparatus is preferably configured, so that no binder material is supplied or can be supplied through it. For example, the required connections can be lacking at a binder material application component or at a binder material supply component. A connection to a binder material accumulator can also be interrupted.

When a binder material is supplied in the second forming device anyhow, the feeding of binder material, however, is adjusted, so that less binder material is supplied than in the first or third forming apparatus. Less binder material means in this context the absolute supply of binder material per second.

According to another embodiment of the invention, an apparatus for producing an absorbing structure is proposed, which includes at least the following components:
- a sifting band for laying plies, preferably air laid plies for forming a ply structure;
- a first forming apparatus, preferably an air laid forming apparatus, through which at least one cellulose material, preferably cellulose fibers, can be extracted;
- a second forming device, through which a binder material, preferably multi-component fibers can be extracted in order to form a first layer together with the cellulose fibers;
- a third forming apparatus, through which a super absorbing polymer SAP, preferably SAP particles and/or SAP fibers, can be laid on the first ply;
- a fourth forming device, through which at least cellulose fibers and a super absorbing polymer SAP, preferably SAP particles and/or SAP fibers, can be laid on the first ply and preferably form a second ply;
- a laying device for a third ply including a cellulose material and a binder material, preferably multi-component fibers;
- preferably an application device through which a binder material, preferably a latex layer, can be applied;
- a heating apparatus, in which bi-component fibers and/or the binding material can be activated;
- a roller assembly, preferably a calender through which the layer structure can be loosely compressed.

A dosing of the SAP particles and/or SAP fibers can vary over a width of the material. Also, there is the possibility to dispose different SAP materials over the width of the material at various locations and also at identical locations, in particular to lay them. An embodiment provides that SAP particles are disposed differently in a layer over a thickness of the material. A position control is performed e.g. through an oriented alignment of the SAP supply. There is also the possibility to perform this position control automatically, e.g. through sensors, image analyzing processing or similar. Also, there is the possibility to test the position of the SAP particles and/or the SAP fibers in the layer automatically, e.g. through detecting the SAP particles and/or SAP fibers. Thus, SAP particles and/or SAP fibers can include e.g. a detectable identifier, e.g. a particular material, a color or another identifier. This facilitates e.g. a correction while the production process is running.

The further processing of the absorbing structures can be performed directly subsequent to the production of the plies. The absorbing structures, however, can also be rolled up while still coherent, or they can be made transportable through a festooning unit. A further processing can then be performed at another location. A further processing can include e.g. a coating, another lamination process with one or more other layers, a cutting in longitudinal and/or transversal direction, another compressing and/or bonding, a stretching or another process step.

Components of an air laid production apparatus and its respective use can be derived e.g. from DE 10 2004 009 556 A1 relating to the production of a fiber web made of cellulose fibers, DE 10 2004 021 453 A1 relating to a forming head, and also a method for producing an air laid layer, from DE 10 2004 056 154 A1 relating to a transport device. Furthermore, a method for producing a fiber fleece according to an air laid method and a fiber suitable for the method can be derived from DE 103 270 26 A1. Furthermore, an air laid method and an air laid ply can be derived from DE 199 183 43 A1, in which air laid ply a bonding fiber is also being used. From WO 2005/080655 A1, in turn, the configuration of an air laid layer with various additional components and their ply arrangement and its ply arrangement and purpose can be derived. A detection of SAP and its controlled dispensing and possible correction and the production of absorbing structures separated from one another can be derived e.g. from WO 03/034963 A2.

Furthermore both non published priority applications U.S. Ser. No. 12/657,987 with the title "Flexible Highly Absorbent Material", inventor Röttger et al. and DE 10 2010 006 228 with the title "Flexibles stark absorbierendes Material" are incorporated in their entirety by this reference.

The documents recited supra and also the documents recited therein state additional options, as to how the device can be configured. In the context of the disclosure of the invention, these printed documents and also the art recited therein are incorporated by reference in their entirety.

The absorbing structure can be used e.g. in a disposable product for hygiene applications. The absorbing structure can also be the disposable article itself.

Preferably, these disposable products are used for baby diapers, female hygiene and incontinence products.

Furthermore, such disposable products can be used in the field of:
- medical products, like e.g. absorber materials and absorber mats; or
- industrial products, like e.g. absorbing materials for receiving liquids.

Thus, the absorbing structure itself can form at least one outer surface, preferably both outer surfaces of a product. The absorbing structure, however, can be at least covered with an additional ply at least on one side, e.g. also on all sides, preferably it can be connected to the ply.

BRIEF DESCRIPTION OF THE DRAWINGS

Further advantageous configurations and improvements of the present invention are described with reference to the following embodiments with reference to the appended draw-

FIG. 8 illustrates the results of the tension tests for determining shear strength in a table.

DETAILED DESCRIPTION

Figure 1:
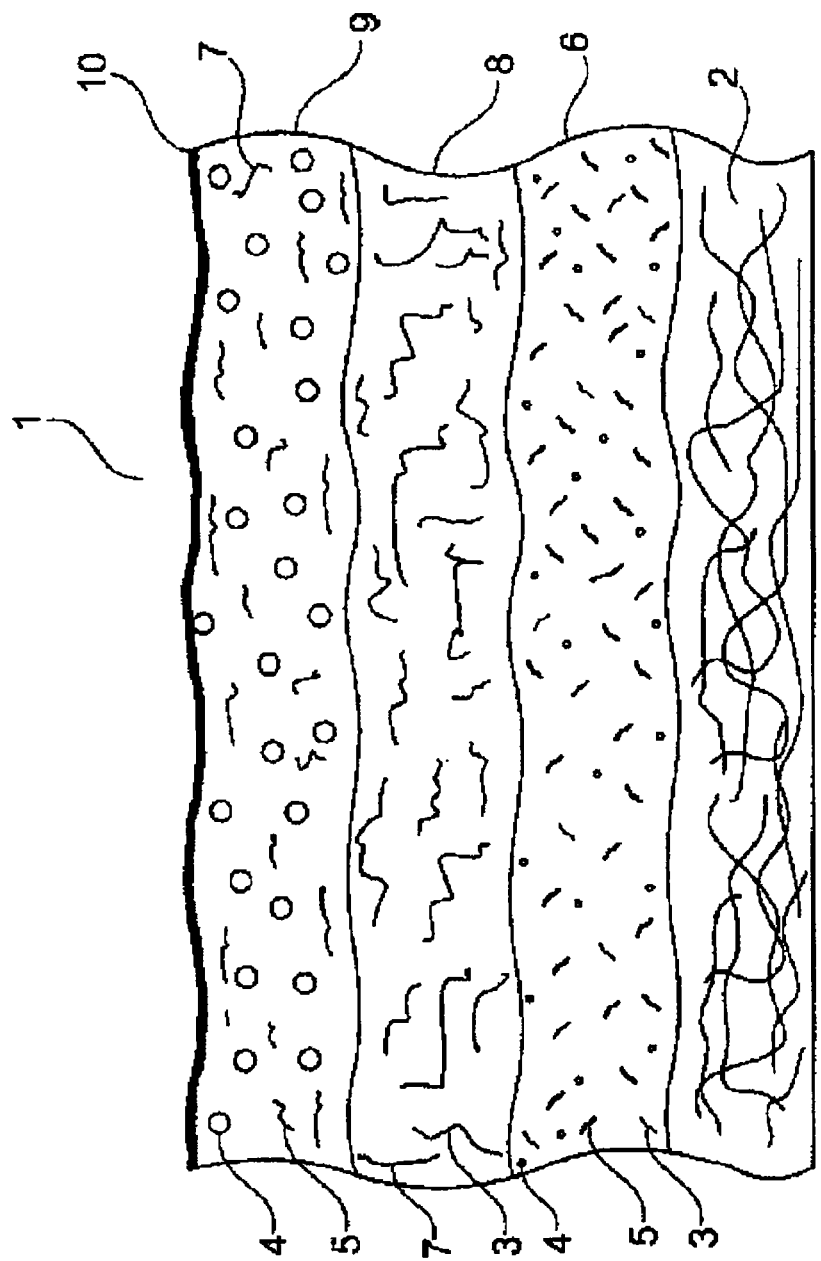
FIG. 1.

The absorbing ply structure 1 illustrated in FIG. 1 includes the following layers:

a support layer 2 which includes a tissue and forms the first ply of the ply structure;

a second ply 6 made of cellulose fluff pulp 3, SAP particles 4 and bonding fibers 5, e.g. bi-component fibers;

a third ply 8 made of cellulose pulp 7 and cellulose fluff pulp 3;

a fourth ply 9 made of cellulose pulp 7, preferably SAP particles 4, which, however, can also be omitted, and binding fibers 5; and a layer made of a binding material 10, e.g. a latex binder.

The plies of the ply structure are disposed on top of one another and connected with one another in a subsequent calendering process using heat and pressure. Thus, the outer plies of the structure are compressed more than the center plies. The ply material 1 can also be configured without the support layer 2. The second ply 6 alone or in combination with the support layer 2 assumes the function of a liquid receiving layer in the ply structure. Due to the SAP particles 4 provided in the ply 6, this ply also has a storage function that is reinforced by the ply 8. The ply 8 includes fluff pulp 3 and cellulose pulp 7. It is only slightly compressed and includes a high volume of voids. The ply 9 includes cellulose pulp 7, bonding fibers 5 and SAP particles 4, and can act as a liquid distribution layer. An outer layer made of binder material 10, e.g. a latex binder, is disposed on the layer 9.

As a function of the selection of the laying and binding process, which is an inline process in this case, the particular layers can have different compression, which is advantageously higher at both outer surfaces of the layer structure than in its inner portion. As described with reference to FIG. 1, the function of the particular layers can also be reversed. Thus, the fourth ply is provided as a receiving ply for liquid, wherein then no SAP is provided in the fourth ply, whereas the support layer configured as a tissue forms a barrier layer, since it has the tightest pores of all plies, and thus the greatest resistance with respect to liquid passage in this case.

Figure 2:
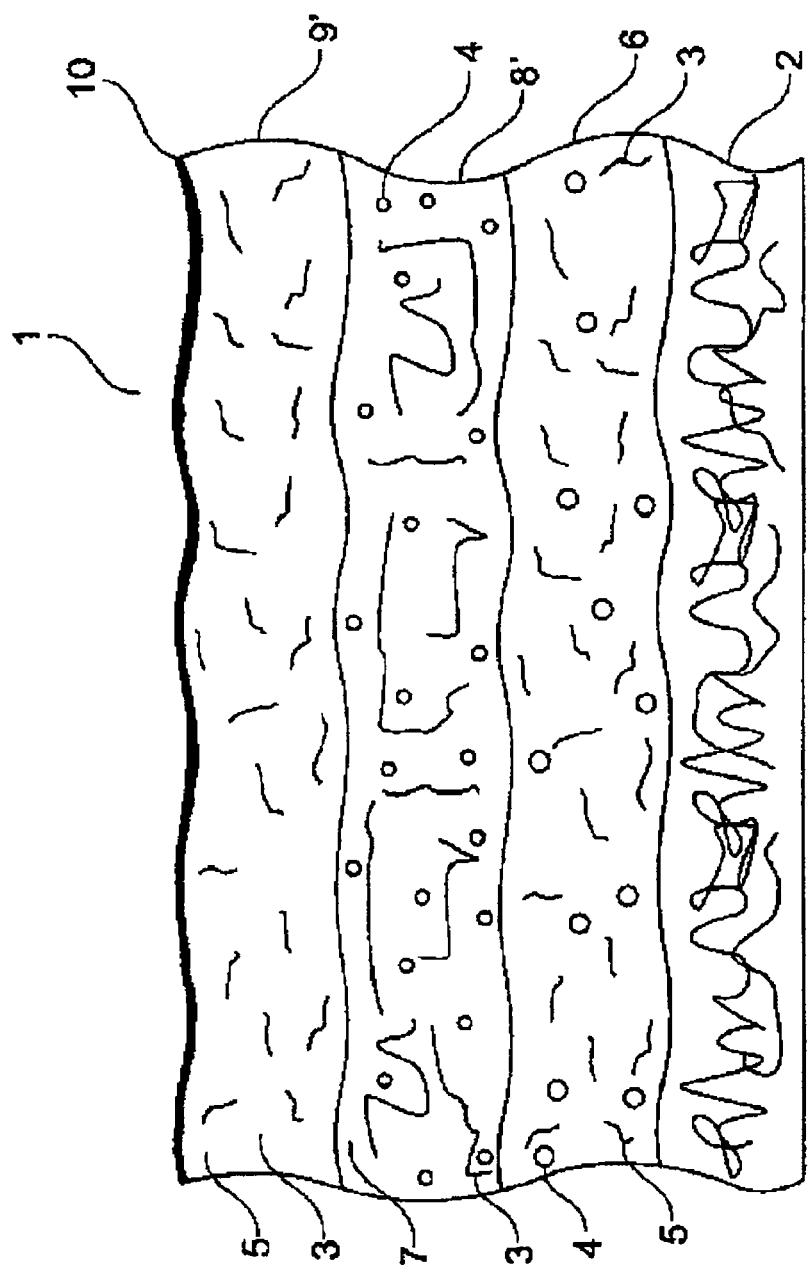
FIG. 2 illustrate schematic views of cross sections of various bonded absorbing structures.

The absorbing ply structure 1 illustrated in FIG. 2 has the following layers:

a support layer 2 which includes a tissue and forms the first ply of the ply structure;

a second ply 6 made of cellulose fluff pulp 3, SAP particles 4 and bonding fibers 5, e.g. bi-component fibers;

a third ply 8' made of cellulose pulp 7, cellulose fluff pulp 3 and SAP particles 4;

a fourth ply 9' made of cellulose pulp 7 and bonding fibers 5; and an outer ply made of a latex binder 10.

The ply 8', based on its composition, preferably includes the cellulose fluff pulp and a very slight compression compared to the adjacent layers. Thus, the SAP particles provided in the ply 8' have high movability in case of a loading through liquid application or shear loading, e.g. by the user. This movability within the ply 8' facilitates decoupling the plies adjacent thereto, so that the plies of the structure are thus movable relative to one another. The SAP particles which are swelled in used condition can slide on one another based on the low compression of the ply 8', thus forming the prerequisite for the sliding effect observed in the ply 8', which prevents a tearing or delamination of the ply structure under load.

Figure 3:
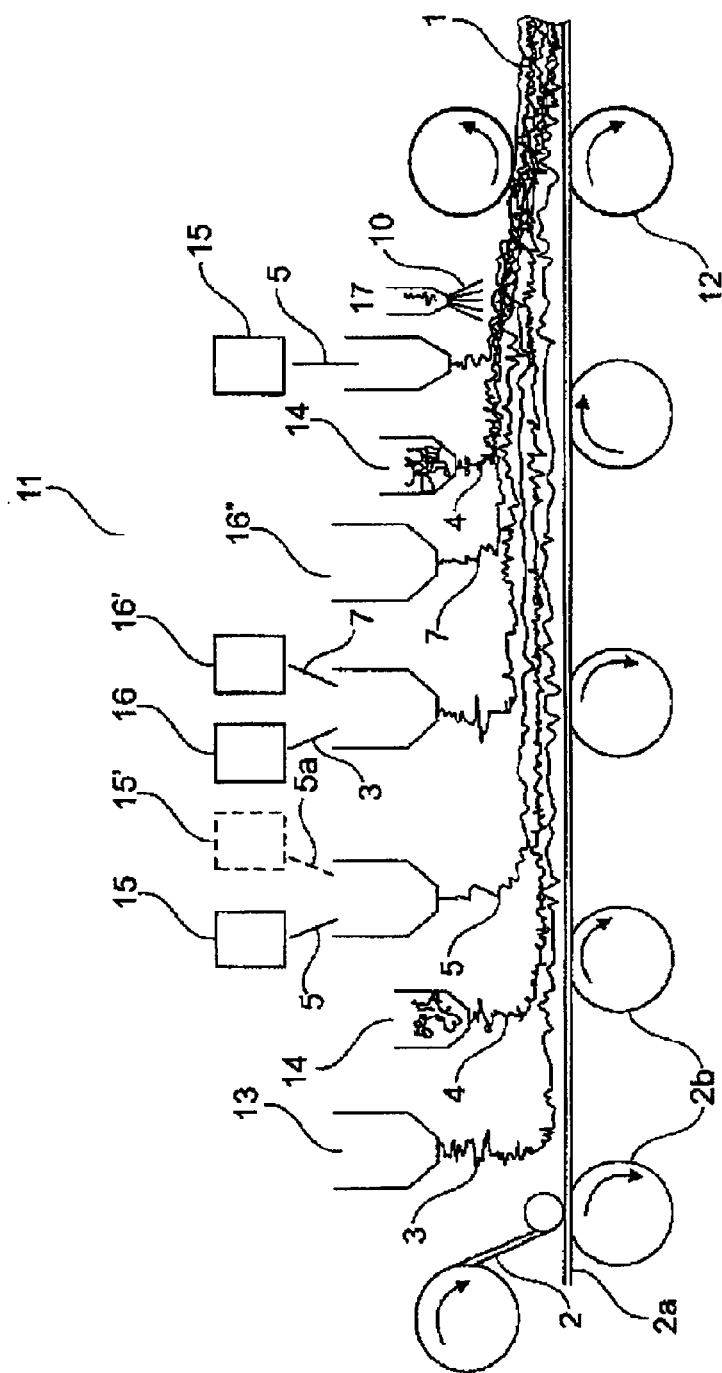
FIG. 3 illustrates a schematic view of a configuration of a production apparatus.

FIG. 3 illustrates a schematic depiction of a possible embodiment for a device 11 for producing an absorbing ply structure 1. An inline process is illustrated with an unwinding apparatus for providing an air laid material 2, which is laid on a sifting band 2a with drive rollers 2b, a first forming apparatus 13 for providing fluff pulp 3, a forming device 14 for providing an absorber, e.g. SAP particles 4, an additional forming device 15, 15' for providing bonding fibers 5, and possibly additional bonding fibers 5a for forming a first ply 6, which is laid on the support layer 2. Fluff pulp 3 and pulp 7 are provided through the forming apparatuses 16 and 16' in order to form a third ply 8, which is laid on the second ply 6. A forming apparatus 16" for providing pulp 7 and forming devices 14 or 15 for providing SAP particles 4 or binding fibers 5 are used for configuring a fourth ply 9, which is laid on the third ply. A binder material 10 e.g. a latex binder is applied to the ply 9 through an apparatus 17, e.g. through application spraying or blade coating. The ply structure can be activated through heat (not shown) after the binder material is applied, and subsequently passes through an apparatus 12 for compressing the ply structure. The apparatus 12 is e.g. a calender with an assembly of smooth rollers, but an infrared heater, an oven section or another heater for activating the bonding fibers can also be provided, which bonds the layers including binder material with one another, but also respectively to one another.

Figure 4:
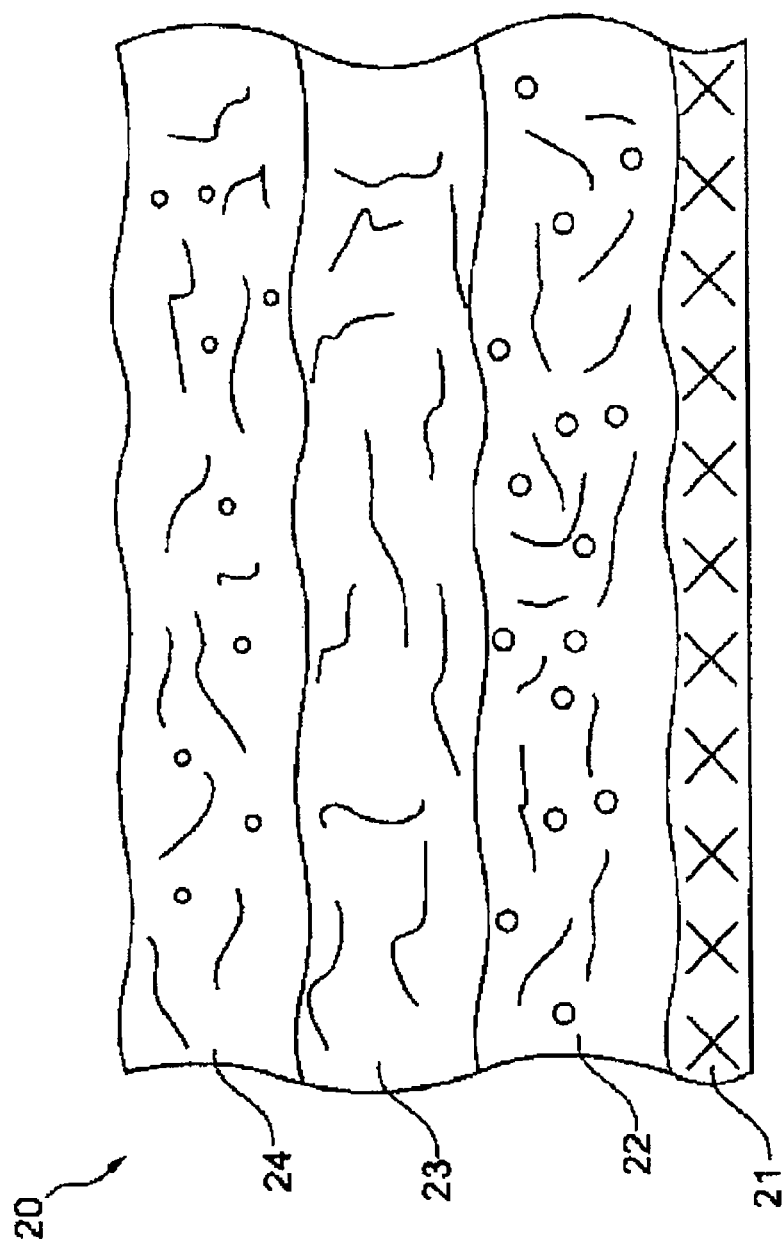
FIG. 4 illustrates a schematic view of another advantageous embodiment of an absorbing structure.

FIG. 4 illustrates another preferred embodiment of an absorbing structure 20 in a schematic view. A second ply 22 is disposed on a paper tissue 21 configured as a first ply. The second ply 22 includes pulp, preferably treated pulp, SAP and a binder material, preferably gluing fibers, e.g. provided in the form of bi-component fibers. The SAP can e.g. also be provided as a particle and/or also as a fiber. The second ply 22 is used as a backup accumulator and can also be used for distributing liquid, which passes through a liquid accumulator disposed there above. The second ply 22 can e.g. facilitate such function e.g. through distributing the SAP, through adjusting the pore size and/or other means. The paper tissue 21 is preferably compressed far enough, so that it acts as a barrier for the liquid included in the second ply and flowing through. Another third ply 23 is disposed on the second ply 22, which third ply is preferably made of pulp, preferably from untreated pulp and/or treated pulp and SAP. Preferably, no binder material is included therein. The third ply 23 is a liquid storage ply. A fourth ply 24 is disposed on the third ply 23. The fourth ply preferably includes pulp, preferably untreated pulp, and a binder material, preferably gluing fibers, e.g. bi-component fibers. Preferably, the fourth ply 24 is made from these materials. Furthermore, the fourth ply 24 acts as a receiving ply, this means it is the first ply to come in contact with the liquid introduced and conducts the liquid to the subsequent plies. The first ply and also the fourth ply 24 are furthermore preferably loaded respectively with additional binder material, e.g. through impregnation, application through a printing (coating) method or through a spraying method or in another manner. Preferably, a latex application is performed respectively. The binder material that is respectively applied to the first ply and to the fourth ply from the outside is preferably the same binder material, in particular the same latex application. An embodiment provides that the binder materials applied to the respective outsides differ from one another. The binder material according to an embodiment is applied in a dosage, so that it only penetrates the first or fourth ply. Another embodiment provides, that it at least essentially only remains at the surface of the first or fourth ply. Another embodiment provides in turn that the binder material penetrates from the first ply 21 into the second ply 22 adjacent thereto, but not into the third ply 23.

PREFERRED EMBODIMENTS

In the subsequent embodiments, the ply structure and its production according to the present invention are described in more detail. As will be described infra, samples according to the invention and reference samples were produced, and subsequently, measurements for determining their thickness, bending length, bending stiffness, tear strength, bonding strength, the liquid absorption capacity and regarding their shear strength were performed.

Two materials A and B were produced using air laid layers according to a proposal for a new absorbing structure. Both materials include three layers, which have been laid on a support layer made from a tissue. After forming this ply structure, a spraying of the two outer surfaces of the ply structure is performed with a dispersion binder material made from a water-based EVA-latex mixture.

The material A (VH460.103) has a weight per area of 460 g/m$^2$ at a thickness of 5 mm (at 0.5 kPa) and a density of 0.092 g/cm$^3$ after a calendering step, while material B (VH600.101) has a weight per area of 600 g/m$^2$ at a thickness of 6 mm and a density of 0.100 g/cm$^3$ for an analogous production process. Thus, a first air laid layer is made of a treated fluff pulp, e.g. biofluff TDR made by Tempec Tartas, thermoplastic bi-components fibers, e.g. HC255 by Trevira or Al-Bounce-Adhesion by FiberVisions, and a SAP with natural extracts developed in particular for urine odor control. A second air laid layer is laid on the top side of the first layer, which air laid layer includes treated fluff pulp, e.g. Tartas TDR, and non-treated fluff pulp, e.g. GP4881 by Georgia Pacific, and the SAP recited supra for urine odor control. On the topside of the second air laid layer, a third layer made of non-treated fluff pulp, e.g. GP4881, and thermoplastic bi-component fibers has been laid.

The layer structures of the samples A and B can include the subsequent typical portions with respect to the composition of the layers.

The tissue portion in the sample A is 3.9% by weight with reference to the total weight of the layer structure. Layer 1 includes 42.9% by weight pulp, 7.1% by weight bi-component fibers and 50% by weight SAP, respectively with reference to the total weight of the layer. The first layer 1 represents 34.6% of the weight of the layer structure. The second layer includes 39.3% by weight pulp and 61.7% by weight SAP, respectively with reference to the total weight of the layer, wherein the second layer 2 constitutes 45.1% of the total weight of the layer structure. The third layer 3 includes 82.1% by weight pulp and 17.9% by weight bi-component fibers, also with reference to the total weight of the respective layer. In the layer structure the third layer 3 constitutes a portion of 13.8% by weight. With reference to total weight the layer structure includes 1.3% by weight Latex respectively on top and on the bottom.

Accordingly, the configuration of the ply structure B with the particular portions of the respective layers, which refer in turn to the entire weight of the particular layer, is as follows:
tissue: 3.0% by weight;
layer 1 with 42.8% by weight pulp, 7.2% by weight bi-component fibers and 50% by weight SAP;
layer 2 with 43.1% by weight pulp and 56.9% by weight SAP;
layer 3 with 75.7% by weight pulp and 24.3% by weight bi-component fibers.

The layer 1 constitutes 34.6%, the layer 2 constitutes 49.0% and the layer 3 constitutes 10.4% by weight of the total weight of the layer structure. Furthermore 1.3% Latex are used on the top and on the bottom of the layer structure.

Latex has been used as follows: A water based EVA-Latex-mix has been used in which Latex constitutes 16% by weight and water constitutes 84% by weight. This dispersion has been used in the layer structures according to samples A and B or VH460.103 and VH600.101.

The bi-component fibers include a titer of e.g. 2.2 dtex and fiber lengths of approximately 3 mm. The core includes PET, while the jacket includes a co-polyolefin or polyethylene. Favor Z 3269 by Stockhausen Inc. was used as a super absorber. Ethylene-vinyl acetate (EVA)-Latex, e.g. Airflex®192, with the designation Vinnapas®192 by Wacker Chemie AG, with ~1.3% dry residue after hardening, the water latex dispersion is used as a latex binder material on the surfaces of the ply structure. An overview of the raw materials used for producing the samples VH460.103/sample A and VH600.101/sample B and their compositions are provided in tables 1 and 2.

The production of the ply structures A and B was performed in the subsequent steps:

The air laid plies were laid as three subsequent layers on the wet laid tissue, which is used as a support material, and an endless fleece was formed. Subsequently, the layer structure was compressed in a roller gap, which was formed by heated smooth rollers. Subsequently, the layer structure was sprayed on both sides with a dispersion binder, the water was extracted, the latex was cross-linked and the melting of the low temperature melting jacket of the bi-component fibers was performed in a multistage drying system. After heating and consolidating the ply structure, the adjustment of the required thickness was performed in a gap of a smooth roller 28 calendar.

The measurement results determined for the samples A, VH460.103 and B, VH600.101 as well as the reference samples MT410.104 and VT500.200 are listed in table 3 for the thickness and in table 4 for the mechanical properties.

The subsequently listed WSP (World Strategic Partners) methods are standardized standard test methods of the European fleece material organization Edana and of the American fleece material organization Inda.

Determination of Thickness:

The thickness is determined according to the standard test method WSP120.6 (05) for the samples A, VH460.103 and B, VH600.101 and for the reference samples MT410.104 and VT500.200 at ten respective particular samples with a size of 7 cm×7 cm respectively. Thus, respectively samples in dry condition, in drenched condition with 10 g of liquid per sample and in saturated condition were measured. The measured values in table 3 prove that e.g. the material VH600.101 according to the invention with a density of approximately 0.1 g/cm³ is configured very loosely in dry condition, which provides more free volume for liquid absorption, and thus its thickness in wet condition does not increase as much as the thickness of the reference material VE500.200, which is more compressed in dry condition than the material VH600.101. Thus, the thickness of the proposed layer structure during liquid absorption is rather constant, which can be considered a comfort feature for use.

Determination of Bending Length and Bending Stiffness:

In order to determine the bending stiffness, the standard test method WSP90.5 (05) was used. Herein, the samples were cut into rectangular strips, whose bending length was measured at the four sides of the strips, and its mean was formed. In order to determine the bending stiffness in mN×cm, the determined bending length in centimeters was multiplied with the respective area weight of the sample and divided by 1000. It can be derived from table 4 that the values for the bending length of the samples in wet state only include approximately 30% to 35% of the values for the dry state for the samples. The stiffness for the samples in wet state, however, only comprises approximately 5% of the stiffness in dry state. The reference samples MT410.104 and VE500.200 illustrate a similar tendency with respect to that property.

Determination of Tear Resistance:

The tear resistance was determined according to the standard test procedure WSP110.4 (05) option B, using a Zwick test apparatus with a clamp distance of 200 mm and a feed of 100 mm/min. According to table 4, the tear resistance of the samples in wet condition decreases to approximately 25% of the value, which was determined for the sample in dry condition (VH600.101), and to approximately 20% of the value for the sample VH460.103. The reference samples MT410.104 and VE500.200 illustrate a lower decrease of the tear resistance from the dry state to the wet state of the samples. Furthermore, the tear resistance values for the sample VH600.101 can be derived from table 4, which were measured for the complete sample, the tissue and the upper side of the sample, which forms the liquid reception layer. Thus, the complete sample has higher tear resistance values than the reference samples. This yields an indication that the outer layers yield the major portion of the tear resistance.

Determination of Bonding Strength:

In order to determine the bonding strength according to WSP401.0, this means the force that is required for tearing the layers apart, samples with a width of 25 mm were provided, and torn up at one side for approximately 3 cm. Subsequently, the clamps have been mounted at their outer plies. Herein, samples were drenched with 10 g of liquid per gram of sample. Samples with a weight of approximately 3 g were evenly drenched with 30 ml of 0.9% NaCl solution, and samples with a weight of approximately 4 g were evenly drenched with 40 ml of 0.9% NaCl solution, and subsequently measured quickly, so that the measurement of the samples was performed in humid state. The side of the samples, which was not yet torn open, was held for support, this means the material was always supported by hand at half the elevation of the clamp distance, so that the high weight of the sample did not falsify the measurement. Table 4 illustrates that the measured values hardly change from dry state to wet state. Contrary thereto, the reference samples MT410.101 and VE500.200 have substantially lower bonding strength in wet condition than in dry condition.

It is being assumed that the sliding effect of the liquid storage layer, which causes a decoupling of the layers of the layer structure, is capable to absorb a certain amount of shear forces and pull forces, thus being able to counteract a tearing or delamination of the sample.

Determination of Liquid Absorption Capability:

The liquid absorption capability was determined according to the standard test method WSP10.1 (05) position 7.2. Thus, five particular samples were used respectively with a size of 10 cm×10 cm. Accordingly, particular samples were made from approximately 6 g of the sample VH600.101. The samples were pretreated by placing them into 0.9% NaCl solution for approximately 1 minute and by having them subsequently drip off for 2 minutes vertically suspended.

In parallel thereto, a method for SAP containing materials developed by the Concert Corp. was used, "CG Test 4 Rev. 5 Test Procedure for Absorption Capacity", dated Mar. 2, 2009. This yields different values compared to the values that have been determined according to the standard test method WSP10.1 (05). For the method developed by Concert, the samples are submerged for 10 min, and drip off vertically for 10 seconds. Using the Concert-method leads to higher values for the liquid absorption capacity of the samples which can be in the range of over 20 g/g, than this is provided for the standard test method recited supra, since the super absorber is configured to bind liquid quickly, but cannot develop its entire absorption capability within one minute.

Table 4 lists the determined masses for the respective samples and their calculated mean values.

The values determined according to the comparison method by Concert are higher than the values for the standard test method.

The liquid absorption capacity LAC in % is determined according to the standard test method WSP 10.1(05) according to the subsequent formula:

$$LAC \% = \frac{M_n - M_k}{M_k} \times 100\%$$

wherein $M_n$ is the mass of the dry sample and $M_k$ is the mass of the wet sample.

Accordingly, the sample VH600.101 has a liquid absorption capacity of approximately 1763% or 17.63 g/g. It becomes evident that the materials according to the invention have a higher liquid absorption capacity than MT410.104 or VE500.200. This effect is explained with a larger move ability of the SAP particles or SAP fibers and the cellulose fibers of the liquid absorption layer, which provides more free volume for liquid during liquid absorption and the associated swelling processes through the existing move ability of the particles.

Determination of the Shear Resistance

The measurements for determining shear resistance were preformed according to the measurement method for the tear resistance. Thus, shearing is interpreted as a type of deformation of a body under the effect of a force, wherein the force acts opposite parallel to parallel inner or outer surfaces of an object. Thus, the surfaces are moved relative to one another. For measuring the shear resistance respective 25 mm wide strips have been cut out of the previously recited samples according to the invention and out of the reference samples, which strips have a length of over 20 cm, typically 26 cm. Thus, all materials were respectively cut to length in machine direction. Subsequently, the samples were grabbed at the outer surfaces of the plies and torn open for approximately 3 cm. This was performed at both ends of the strips.

Initially, the samples were clamped respectively without using a tape, so that the one opened outer layer, e.g. the material upper side was clamped in the upper clamp and the other outer layer, this means the material bottom side remained loose under the upper engagement clamp. Subsequently, the opened outer layer of the side opposite to the upper end, thus the material bottom side was clamped into the lower clamp and the other outer layer, thus the material upper side remained loose above the lower engagement clamp.

As expected, the coherence of the samples VH460.103 and VH600.101 in the inner layer made of pulp and SAP was not as high as the tear resistance of the outer layers, this means of the tissue supported pulp-SAP-bi component bottom side reinforced with hardened latex binder. For the sample VH600.101, tear resistance on the side where the tissue is disposed is approximately ¾ of the measured tear resistance and the tear resistance of the upper side of the ply structure which includes a bi component layer with hardened latex binder provides approximately ¼ of the total tear resistance, while the inner layer, which does not include binding fibers, thus hardly contributes to the tear resistance. There were hardly any differences found between measurements with and without tape.

In order to be able to also measure the reference materials, applying tapes was necessary, since the opened outer layers at these samples prematurely tore off during clamping and starting of the movement according to the method recited supra. By applying tape to the upper and under side of the samples the premature tearing of the outer layers was prevented, since the tear resistance of the tape at 45 N/cm is above the shear fracture force of the materials and the outer layers have thus been effectively fixated against tear off.

Gluing Tesapack® 4024 PP, brown variant, onto the samples was performed in the subsequent steps:

First the samples in a typical A4-hand sample size were glued in longitudinal direction with a 5 cm wide tape, so that the tape entered on adhesion bond with the surface of the sample. Subsequently, the 25 mm wide strips were cut analogously to the previously recited mechanical standard measuring methods for tear resistance, bending stiffness and bonding strength with a standard cutting apparatus to a length of typically 26 cm. Subsequently, the samples glued with tape on both sides were opened in the center and torn open for approximately 3 cm, as provided for measuring the bonding strength according to WSP401.0, however, the tearing open is performed on both ends of the strip. Like previously for the tests without using tapes, the clamping was performed in an alternating manner at the opposite ends, while the one end remained loose within the clamp distance, so that it does not contribute to shear resistance and only the shear force in the center layer is determined.

High and unfavorable values for the shear fracture force were observed for the reference materials. Thus, the value for MT 401.104 was at 37 N, which is presumed to be a consequence of the thermal bonding of the pulp and the bi component fibers in combination with the SAP particles of the inner layer. A shear force of 44 N was determined for the reference material VE 500.200 which is caused by a high density and strength, in particular also in the interior of the ply structure. Contrary thereto, 5-6 N were determined for the sample VH 600.101 according to the invention and 4 N were determined for the sample VH 460.103. The measurements show that the samples according to the invention can be moved more easily relative to one another even in dry state and thus provide the advantage of the movability of pure pulp-SAP-materials in the interior of the ply structure, wherein, however, the strength in the outer layers provides the desired comfortable textile properties.

A combination of free absorption and mechanical surface strength in wet condition sets the layer structure according to the invention apart from the purely mechanically compressed cellulose-SAP-airlaids as they are known e.g. from McAirlaid's and Rayoniers EAM. These layer materials do not have sufficient wet integrity and thus are similar to the properties of so called "airfelt pads".

Compared to homogenously thermally bonded airlaid materials like e.g. the reference material MT 400.101, the deformation of the ply material according to the invention in wet condition is reversible which causes reduced stiffness of the ply structure. Furthermore, the material has sufficient flexibility also in dry condition through large pores in the center of the ply structure; this means that the cantilever bending stiffness for this material also in dry condition is lower than for thermally bonded products with a stiff matrix.

Tension Tests for Determining Shear Strength:

Further testing with prepared samples was performed as an extension of the tests described supra for determining shear strength or shear fracture force for the samples A (VH 460.103) and B (VH 600.101) and the reference samples MT 410.104 and VE 500.200. Subsequently, the tests procedure is lined out in general and thereafter it is described in detail. A preparation of the samples or of the air-laid fleece material is provided so that all samples are sprayed on both sides with a spray glue and also glued on both sides with an adhesive tape after a drying time. Loading the samples with the spray on glue provides a permanent connection between the sample and the adhesive tape, wherein a permanent connection is also provided in wet condition of the samples. Samples thus prepared therefore provide a determination of a wet shear strength. The measurements for determining the wet shear strength were performed analogous to the fracture strength measuring method. Thus, shearing is a deformation of a body under impact of a force, wherein the force impacts parallel inner and outer surfaces of a body in opposite parallel direction. The surfaces of the samples are thus moved relative to one another. For measuring the shear strength, samples A and B and the reference samples with a width of 25 mm respectively and a length of over 20 cm, typically 26 cm have been cut out of the prepared air-laid fleece cloth materials. Thus, all materials were respectively cut to length in machine direction so that the samples were provided as strips.

Figure 5:
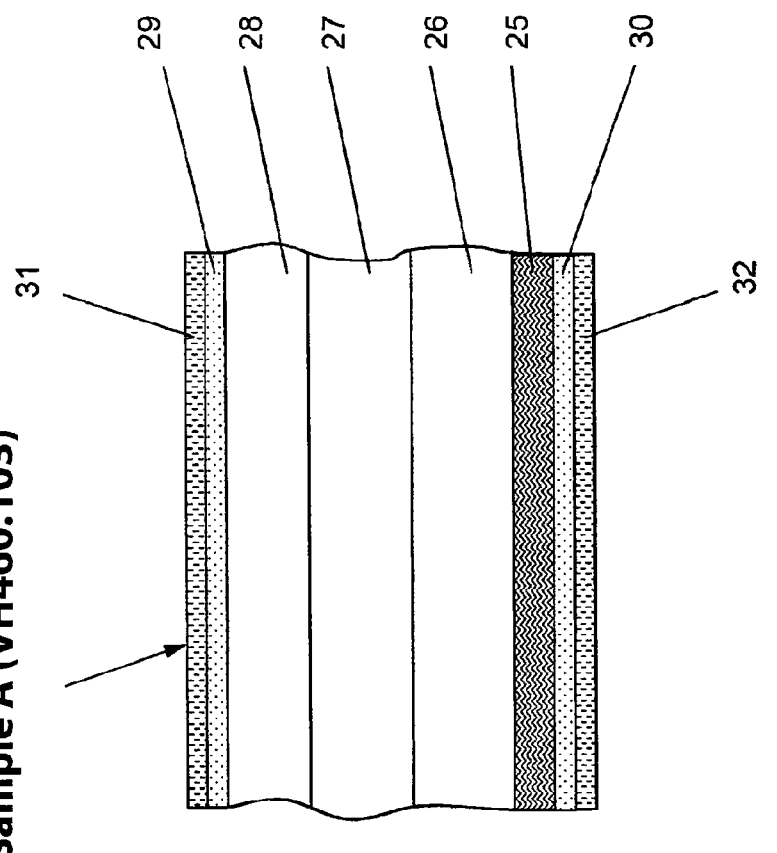
FIG. 5 illustrates a schematic view of a sample A with a designation VH 460.103 in a sectional view and in a lateral view in longitudinal direction.

In FIG. 5, the sample A with a sample designation VH 460.103 is schematically depicted in a sectional view and in a lateral view in longitudinal direction. The sample A includes a carrier layer 25 made from a tissue material on which a liquid absorption layer 26 was deposited. The liquid absorption layer 26 is formed from treated fluff-pulp; particle shaped SAP material and thermoplastic bi-component fiber and forms a first air-laid layer. A liquid storage layer 27 is applied to the liquid absorption layer 26 in order to form another air-laid layer. Thus the liquid absorption layer 27 includes treated fluff-pulp and SAP particles. The liquid storage layer 27 preferably does not include thermoplastic bi-component fibers. Above the liquid storage layer 27, another liquid distribution layer has been applied which also forms an air-laid layer. On both sides, the layer structure was impregnated with a dispersion glue, also designated latex binder. The binder application made from ethylene vinyl acetate (EVA) latex, for example Airflex®192, with the designation Vinnapas®192 by Wacker Chemie AG, is performed over the entire surface. After drying and hardening the water-latex dispersion, approximately 1.3% remain per side. This corresponds to 6 g per square meter dry residual on each side at 460 GSM. The latex binder layers 29, 30 were depicted as hatched surfaces. Thus, it is appreciated that the thicknesses of the layers are only sketched. For example the thickness of the latex layers 29, 30 deviates from the actual conditions. Thus, it is possible in particular that the latex binder is only applied to the liquid distribution layer 28 and/or penetrates portions of the liquid distribution layer in a dispersive manner and forms a binding agent layer in the liquid distribution layer 28. This applies accordingly for the latex binder layer 30 applied to the tissue layer 25, wherein the latex binder layer 30 is also illustrated in a highly enlarged manner. Overall, the sample has a thickness of approximately 5 mm.

The sample A was prepared as follows for shear strength value tension tests. The sample A includes a layer structure made from tissue 25 impregnated on both sides with a latex binder, a liquid absorption layer 26, a liquid storage layer 27 and a liquid distribution layer 28. The layer structure was sprayed on both sides with spray glue "UHU® 3-in-1", 500 m can, product number UH48905, available in the UHU® Profishop. The spraying is performed on two sides in three respective spraying lines, thereafter the spray glue is dried off for ten minutes. The permanently gluing variant of the spray glue was used which is being sold under the designation "UHU® 3-in-1, first variant, permanent". Per side, three horizontal spray lines are applied after positioning the strip with the longer side in horizontal orientation, this means spray lines at a distance from the air-laid layer of 20 to 25 cm according to the processing instructions on the spray glue can in the center longitudinally overlapping horizontally from the left to the right, then from the right to the left and eventually again from the left to the right. The simple dosage per surface area is approximately 200 ml/m$^2$ for three spray lines that are arranged on top of one another, thus 600 ml/m$^2$ are applied. After drying off, the layer structure was glued on both sides with a tape 31, 32 that is 5 cm wide. For a tape, the tape with the designation Tesapack® 4024 PP, variant brown, a PP film with acrylate glue mass, available at TESA SE, a Beiersdorf company was used. In order to obtain a defined rolled weight, the sample A was rolled once with a brass roller with a weight of 7.4 kg. From the layer structure thus prepared, samples with a length of 260 mm and a width of 25 mm were cut.

Figure 6:
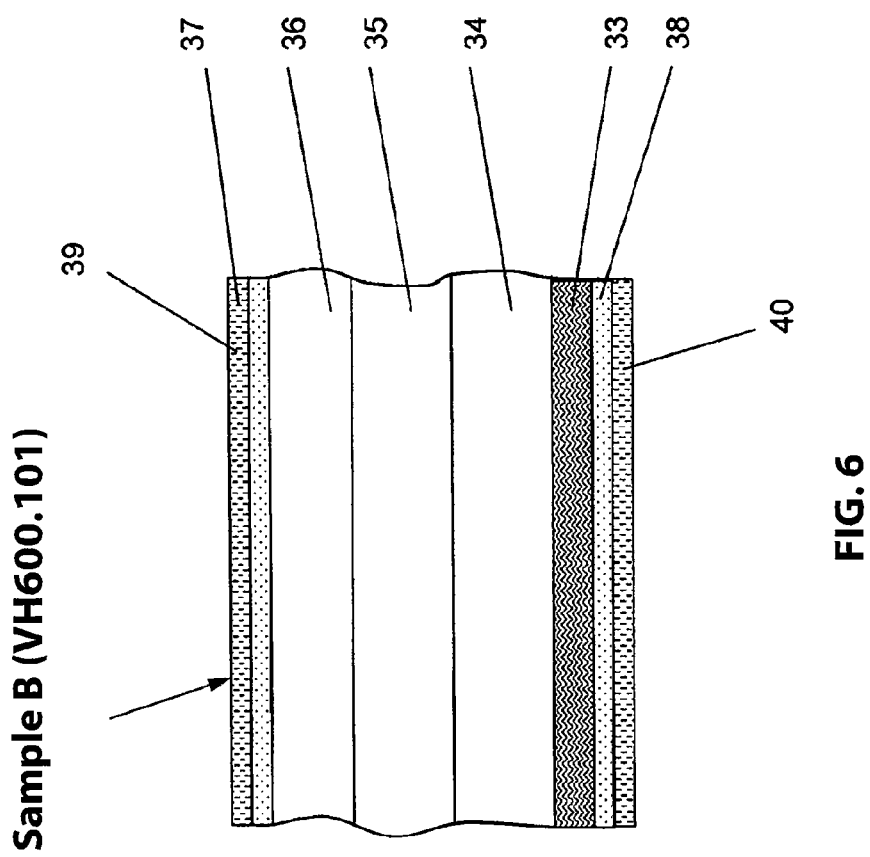
FIG. 6 illustrates a schematic sectional view of a sample B with a designation VH 600.101 in cross section and in a lateral view.

FIG. 6 illustrates a schematic sectional view of a sample B with the designation VH 600.101 in a cross-sectional view and in a lateral view. The sample B includes a carrier layer 33 which is a tissue layer and on which a liquid absorption layer 34 was placed in an air-laid method. The liquid absorption layer 34 includes treated fluff-pulp, SAP particles and thermoplastic bi-component fibers. Preferably the liquid absorption layer 34 includes these components, as they are also included for the instant measurement. A liquid storage layer 35 was also placed onto the liquid absorption layer 34 through an air-laid method. The liquid storage layer 34 includes treated fluff-pulp and SAP particles, preferably the liquid absorption layer 34 includes these components and they are also used for the instant measurement. Above the liquid storage layer, a liquid distribution layer 36 was deposited, wherein the liquid distribution layer is formed from untreated fluff-pulp and thermoplastic bi-component fibers. The layer structure including the carrier layer 33, the liquid absorption layer 34, the liquid storage layer 35 and the liquid distribution layer 36 is provided on both sides with a binder layer 37, 38 made from latex. The binder application including ethylene vinyl acetate (EVA) latex, e.g. Airflex®192 with the designation Vinnapas®192 by Wacker Chemie AG is provided over the entire surface. After drying and curing the water-latex dispersion, approximately 1.3% remains per side. This corresponds at 600 gsm, to approximately 7.8 gsm dry residual on each side. In order to prepare the sample B for tension tests for determining shear strength, the layer structure provided with the binder was sprayed with a spray glue like sample A, wherein the spray glue is sold under the designation UHU 3-in-1, first variant permanent. Due to the thickness of the spray glue that is negligibly small with reference to the layer structure, the spray glue layer is not illustrated. After ten minutes of drying the spray glue, the layer structure was glued with tape 39, 40 on both sides. For a tape 39, 40 like in the sample A, the tape 39, 40 with the designation Tesapack® 424 PP variant brown with a width of 5 cm was used. After gluing the glued layer structure was rolled with a brass roller with a weight of 7.4 kg in order to obtain a defined weight. From the prepared sample material, samples with a length of 260 mm and a width of 25 mm were cut for tension tests.

The spray glue maintains a permanent connection between the layer structure that is provided with binder material and the adhesive tape. This assures the measurement, this means performing tension tests for determining shear strength also in wet condition of the samples.

As recited supra with respect to the samples, sample A differs from sample B with respect to the composition of the layers of the liquid absorption layer, the liquid storage layer and the liquid distribution layer. Thus, in particular the liquid storage layer of the sample A is formed from 39.3% by weight fluff-pulp and 61.7% by weight SAP particles, whereas the liquid storage layer of sample B is formed from 43.1% by weight fluff-pulp and 56.9% by weight SAP particles. Also with respect to the configuration of the liquid distribution layer, the samples A and B differ from one another when the liquid distribution layer 27 of sample A has a percentage of 82% by weight fluff-pulp and 17.9% by weight bi-component fibers, the liquid distribution layer 36 of sample B is formed from 75.7% by weight fluff-pulp and 24.3% by weight bi-component fibers. An essential difference between the samples A and B and the reference samples MT 410.104 and VE 500.200 is that the samples A and B have a liquid storage layer 27, 35 which does not include bi-component fibers.

The fluff-pulp cellulose fibers of the liquid storage layer are not impregnated with a binder, or they do not include a binder. The non-presence of a binder facilitates that the SAP particles included in the liquid storage layer 27, 35 can swell almost unimpeded and/or can move towards one another when loaded with gravity which provides a motion degree of freedom to the liquid storage layer.

Besides the methods for preparing the samples A and B described with reference to FIGS. 5 and 6, also the samples C and D were used for tension tests in which using spray glue on the binder layer was omitted, wherein the samples C and D however coincide in other features with the described samples A and B. One reference sample C (MT 410.104) is thermally bonded without using a binder like Latex. Rather, the properties of bonding fibers configured as bi-component fibers are being used. The second reference sample D (VE 500.200) on the other hand side uses a binder in the form of a dispersion binder including Latex. The reference materials essentially include three layers:

The material MT 410.104 after a calendaring step has an area weight of 410 g/m$^2$ at a thickness of approximately 5.4 mm (at 0.5 kPa). Thus, a first layer includes an air-laid layer made from an untreated fluff-pulp, e.g. NB 416 by Weyerhaeuser with thermoplastic bi-component fibers, e.g. HC 255 by Trevira. On the top side of the first layer a second layer in the form of an air-laid layer with an untreated fluff-pulp, e.g. NB 416 by Weyerhaeuser and a super absorber, e.g. FAVOR by Evonik Stockhausen have been deposited. On the top side of the second layer, a third layer made from untreated fluff-pulp, e.g. NB 416 by Weyerhaeuser and thermoplastic bi-component fibers, e.g. HC 255 by Trevira has been deposited.

The layer structures can have the following typical portions with respect to composition of the layers:

Layer 1 includes 82.8% by weight pulp and 17.1% by weight bi-component fibers respectively with reference to the total weight of the layer. The second layer includes 39.1% by weight pulp, 9.7% by weight bi-component fibers and 51.2% by weight SAP respectively with reference to the total weight of the layer. The third layer includes 74.4% by weight pulp and 25.6% by weight bi-component fiber, also respectively with reference to the total weight of the layer. The layer portions of total weight of the layer structure are as follows: layer 1=29.2% by weight; layer 2=51.3% by weight; layer 3=19.5% by weight.

The values and compositions for the material VE 500.200 however are as follows:

The material VE 500.200 after running through an embosser with a particular embossing pattern and a calendaring step has an area weight of 500 g/m² at a thickness of approximately 1.6 mm (at 0.5 kPa). Thus, a first layer includes an air-laid layer made from a treated fluff-pulp, e.g. GP 4821 by Georgia Pacific or Biofluff TDR by Tembec Tartas. On the top side of the first layer a second layer including an air-laid layer with an untreated fluff-pulp, e.g. NB 416 by Weyerhaeuser and super absorber, e.g. EK-XEN 52 by Ecotech has been deposited. On the top side of the second layer a third layer made from treated fluff-pulp, e.g. GP 4821 by Georgia Pacific or Biofluff TDR by Tembec Tartas has been deposited. After forming this layer structure, a spraying of the two outer surfaces of the layer structure is performed with a dispersion binder made from a water based EVA latex mixture, wherein a latex portion was 4.5% by weight and a water portion was 95.5% by weight.

Accordingly, the configuration of the reference sample VE 500.200 with the portions of the particular layer which respectively refer to the total weight of each single layer is as follows:

Layer 1 with 100% by weight pulp,
Layer 2 with 25.3% by weight pulp and 74.7% by weight SAP;
Layer 3 with 100% by weight pulp.

The layer portions of total weight of the layer structure are as follows: layer 1 13.8% by weight; layer 2 65.9% by weight; layer 3 16.3% by weight besides respectively 2.0% by weight latex dry residual on top and on the bottom after the water portion is no longer present.

Figure 7:
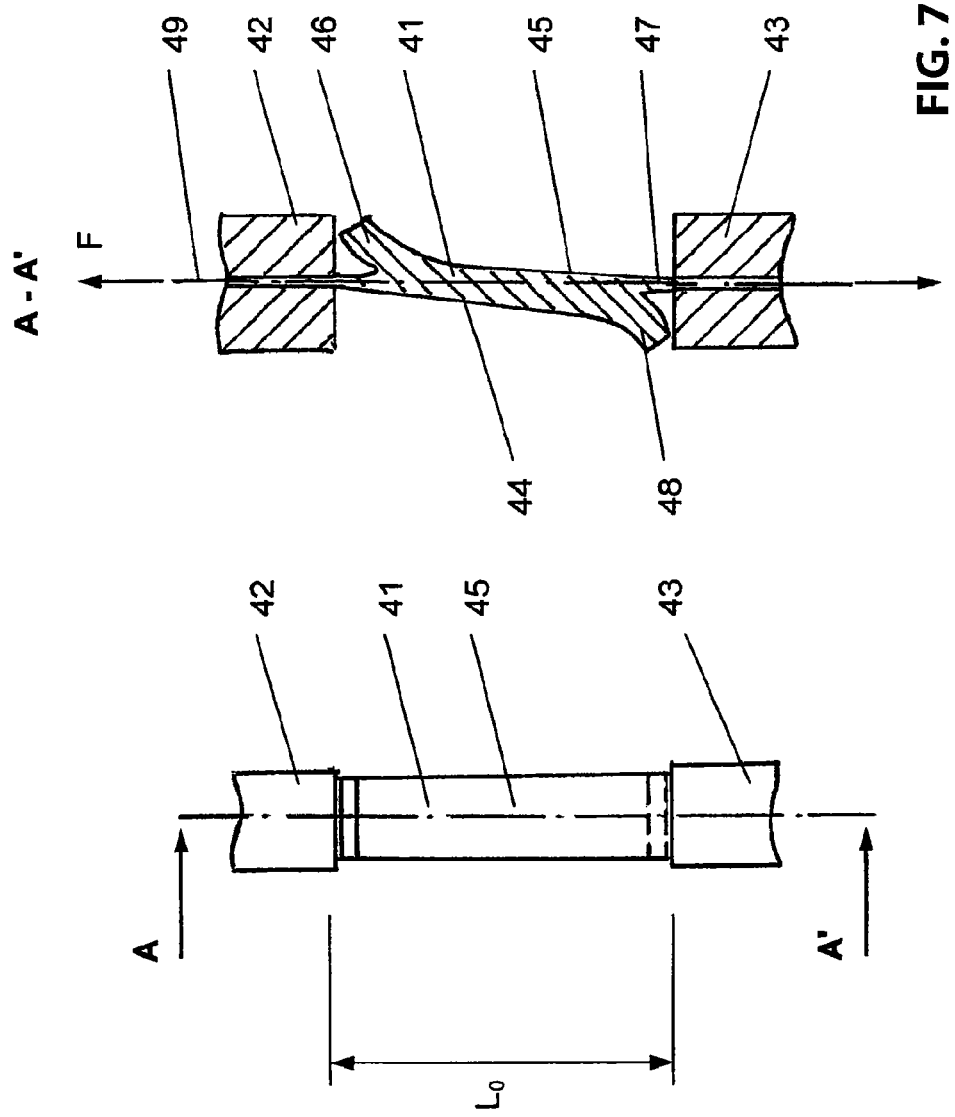
FIG. 7 illustrates a principle view of a sample clamped between jaws of a tension tester.

FIG. 7 illustrates a principle illustration of a clamping of a sample 41 between clamping jaws 42, 43 of a measuring device for tension tests. Thus, for a measuring device, a machine by the Zwick company from Ulm was used with a designation Zwick/Roehl with a length change sensor type BZ 2.5/PN 1S. This is a machine configured to capture a tension-extension diagram in the mode constant rate extension (CRE).

A standardized measuring method for determining a fracture and/or pull force and extension for non-woven materials forms the basis for these tests. The standardized test is designated with WSP 110.4 (05). The standard test designates a test for determining an extension and a pull force for non-woven materials and can also be designated as "Standard Test Method for Breaking Force and Elongation of Nonwoven Materials (Strip Method)". It is measured in CRE mode (constant rate of extension); that means the extension of the length rate of the probe is proportional to time. Generally, the option B with the following changes is selected. The samples or test specimens used in the standard test under option B have a width of 50 mm and a length of 200 mm. Differently from the standardized test, samples with a width of 25 mm and a length between the clamping jaws of $L_0$=200 mm were used for tension tests, this means during the tension test, the clamping length was 200 mm. Furthermore, testing was done with a preload force of 0.5 N and a test velocity of 100 mm/min. The testing was done under laboratory conditions at 23° C. and 50% relative humidity plus normal tolerances. The clamping length $L_0$=200 mm is recorded in FIG. 7 in top view of the clamping jaws 42, 43 and the sample 41. The width of the clamping jaws is 60 mm so that the samples with their width of 25 mm are well received for central clamping.

The right illustration in FIG. 7 illustrates a schematic cut along the line A-A' and illustrates the clamping of the sample 41 between the upper and lower clamping jaws 42, 43 of the measurement device. The samples A and B and the reference samples MT 410.104 and VE 500.200 were all respectively cut to length in machine direction. Subsequently, the samples were gripped at the outer surfaces 44, 45 of the layers and torn up by approximately 3 cm in the center cutting the thickness in half. This is performed at both ends of the samples 41.

As illustrated in the right depiction of FIG. 7, the outer layers that were disengaged and provided with adhesive tape were respectively clamped so that the first opened outer layer 44, for example the material upper side, was clamped in the upper clamping jaw 42 and the other outer layer 46, this means the lower material side remained loose under the upper clamping jaw 42. Subsequently, the open outer layer 47 of the side opposite to the upper end, thus, the lower material side 45 was clamped into the lower clamping jaw 43 and the other outer layer 48, thus, the material upper side 44 remained loose above the lower clamping jaw 43. The clamp condition of a sample 41 is illustrated in unloaded condition before the beginning of the tension test. As apparent and illustrated by the symmetry line 49, the sample 41 goes through a shear loading in the portion of the liquid absorption layer, the liquid storage layer and the liquid distribution layer. The following test series were performed.

In a first test series, the samples 41 were clamped in dry condition and loaded with a pull force in a direction of the arrows F. The tests were performed three times.

In a second sample series, in turn, three tension tests were performed, wherein the samples 41 were prepared through a one-minute submersion into a 0.9% NaCl solution. After submersion, the samples 41 were able to drip off for two minutes, which in turn corresponds to the standardized test method WSP 10.1, absorption.

In a third tension test series, three tension tests were performed again. Thus, the samples 41 were submerged for ten minutes into a 0.9% NaCl solution and were allowed to drip off subsequently for ten seconds in a vertical position. This corresponds to the Concert CG-test 4 Rev. 5 procedure for the absorption capacity dated Mar. 2, 2009.

FIG. 8 depicts the results for the pull tests for determining a shear strength as table 5. The test results 1 through 9 illustrate tests with the samples C and D and the reference samples MT 410.104$_{ohne}$ and VE 500.200$_{ohne}$ which were reinforced with a tape at the outer layer, wherein the outer layer, however, is not sprayed with spray glue. The designation tr. thus designates samples in dry condition and the designation n. stands for samples in wet condition.

The tests with the running number 10 through 45 are tests which were performed after one minute wetting and after ten minute wetting.

The samples A, C (VH 460.103) and B, D (VH 600.101) configured according to the invention were compared with the reference samples MT 410.104, MT 410.104$_{ohne}$ and VE 500.200, VE 500.200$_{ohne}$. The tension tests are sequentially numbered from 1 through 45. The tension test with the number 1 describes a tension test with a sample D configured according to the invention in dry condition, wherein the sample D was glued with adhesive tape at the outer surfaces. The sample was clamped into the measuring device as described supra and illustrated in FIG. 7 and loaded with a force F. Through clamping the opposite outer layers, the tension test was used for determining a shear strength value of the layer structure. The maximum shear strength value for the sample D in test number 1 was at F max=6.82 N/25 mm for a movement distance of the clamping jaws of a total of 9.19 mm which corresponds to an extension of 4.58% with reference to the clamping length $L_0$. Thus, the extension is computed from the ratio:

Extension=$\Delta L/L_0$[in %].

Thus, $\Delta L$ is the distance that has to be covered by the clamping jaws until the maximum force is reached and the sample is eventually fractured.

The pull test with the running number 2 was performed with a wet sample D, wherein the sample was sprinkled on its sides. A measure for the humidification was the weight of the sample D, wherein 10 ml of a 0.9% NaCl solution were supplied per gram of sample weight. Thus, the sample D was supplied with 40 ml of 0.9% NaCl solution according to pull test number 2. The small shear strength of F max=6.82 N that was determined in tension test 1 was reduced by humidifying the sample, wherein a small shear strength of F $max_1$=5.06 N was also determined in tension test number 2. Also the pull test number 3 for the sample D which was also performed in wet condition confirms the small shear strength which is also very small at F $max_3$=5.65 N. The measurements of the pull tests number 1 through 3 show that the samples according to the invention in dry and in wet condition can be moved parallel to one another very easily.

The value of the shear strength refers to a sample width of 25 mm for all samples.

The sample C which was analyzed in dry condition in the pull test number 8 had a maximum shear strength of F $max_8$=11.66 N. This value which is also small was almost cut in half in wet condition according to the pull test number 9 down to F $max_8$=5.65 N. It is also appreciated that also the covered distance for reaching the maximum pull force for the sample B was more than cut in half and also almost cut in half for the sample A. The samples C and D configured according to the invention have a lower shear strength which in turn represents an advantage with respect to the movability of the layers relative to one another.

Differently from the samples C and D configured according to the invention, the reference samples according to pull tests 4 through 7 have a very high shear strength of F $max_4$=34.94 N and F $max_6$=41.26 N. With reference to movability, this means that very high forces are required in order to move the layer structure of the reference samples internally. The reference sample MT 410.104 in wet condition still has a high shear strength, but the shear strength of the reference sample VE 500.200$_{ohne}$ in wet condition (pull test number 7) is significantly reduced and is in the range of the samples A and B according to the invention at F $max_7$=5.59 N. The reference material VE 500.200$_{ohne}$ does not include melt glue fibers for wet connection and the surface binder does not act in the inner layer. Thus, the absorption material can swell up and facilitates easy movement of the layers relative to one another. The lacking melt glue fibers in the reference sample VE 500.200$_{ohne}$ affect the movability of the layers relative to one another in a positive manner so that a movement of the layers relative to one another in wet condition can be provided.

The pull tests numbers 10 through 18 illustrated in table 5 of FIG. 8 illustrate the results of the pull tests in dry condition and in wet condition of sample A according to the invention. The samples were sprayed with spray glue and provided with tape for reinforcing the outer layer. When the pull tests 10, 11 and 12 performed in dry condition have higher shear strength compared to the test number 8 performed without spray glue, then this slightly increased shear strength value is caused by using the spray glue. In wet condition, however, the shear strength value decreases again significantly and based on values between F $max_{13}$=5.16 N and F $max_{14}$=4.18 N is still below the values of the pull test 9 without spray glue. When the sample A as shown in tests 16, 17 and 18 is subjected to humidification over a longer time period, the shear strength values drop again significantly.

When the sample A is submerged for ten minutes in a 0.9 NaCl solution as performed in the pull tests 16 and 18, the SAP particles have sufficient time to absorb moisture and to swell. Due to the lack of bonding fibers in the liquid storage layer, the super absorber material (SAP) can swell freely, this means it is almost not prevented from free swelling. After swelling, the SAP particles act like a "lubricant" or the liquid storage layer overall acts like a sliding layer between the liquid absorption layer and the liquid distribution layer. As clearly evident from the test number 16, 17 and 18, the longer swelling time of the absorbing particles reduces the shear strength values.

The pull tests with numbers 19 through 27 show pull tests for determining shear strength values for sample b configured according to the invention. The samples B were sprayed with spray glue and fixated with adhesive tape at the outer layers. The samples B for manufacturing reasons have a thicker liquid storage layer, this means a thicker center layer which also does not include bi-component fibers. The thicker liquid storage layer causes easier movement of the layer structure in dry condition which is reflected in table 5 in the pull tests with numbers 19 through 21. The shear strength of sample B in dry condition which is already very small is reduced even more through humidification and has maximum tensile strengths of below 3 N after ten minute humidification. When on the one hand side the configuration and in particular the thicker liquid storage layer has a positive effect upon the movability of the layer structure, the movability is further increased through humidification of the absorbing particles and their "sliding effect" after an almost unimpeded swelling of the layer structure.

The pull tests of the first reference sample MT 410.104 are reflected in the pull test numbers 28 through 36. It is clearly visible that based on high shear strength in dry condition of significantly more than 30 N, the shear strength in wet condition decreases only slightly. When the reference sample according to pull test 28 has a shear strength of F $max_{28}$=30.09 N, the value drops after one minute of wetting of the sample only to F $max_{31}$=19.4 N. The reference sample MT 410.104 has a high resistance against shear loading in dry condition and also in wet condition. The layers of the structure can thus only be moved relative to one another when high forces are being applied.

The pull tests according to numbers 37 through 45 depict the reference samples VE 500.200 in dry condition and also in wet condition and the results of these tests. In dry condition, the reference sample as stated e.g. in pull test number 37 has a maximum pull force of F $max_{37}$=50.73 N. The shear strength values decrease strongly until integrity in wet condition is lost. The reference sample has no melt glue fibers for wet bonding so that a significant drop of the shear strength values is provided in wet condition. This significant drop to an eighth of the original shear strength was confirmed in the pull tests with numbers 6 and 7, herein wet means sprinkling with 10 ml/g. A post measurement with complete immersion in 0.9% NaCl solution for 1 min and 10 min confirms the strong drop of the wet shear strength values. The integrity of the layer interconnection is not provided anymore as apparent from tests 40 through 45.

In particular the measurement values from table 5 also show the following context: with the proposed concept it is possible to obtain an integrity of the layer structure which on the one hand side is provided in dry condition so that the layer structure is easily bendable and flexible and thus can adapt well to a contour. In particular this structure is not stiff which can be the case otherwise for layer structure which have high strength. On the other hand side in wet condition, this means when actually using the layer structure through liquid absorption the integrity of the layer structure is still provided so that it does not fall apart. This applies in particular also when liquid has a longer impact time. Thus in particular a layer structure can be provided which remains flexible on the liquid impact and which does not become stiffer.

For example the following results have proven advantageous when configuring a proposed layer structure.

Thus, one embodiment can provide that an absorbing structure has a ratio of a shear strength of a sample with a width of 25 mm and a clear clamping length of 200 mm from a wet condition into a dry condition in a range of 1 to 1.2, preferably 1 to 2 up to a ratio of 1 to 4, wherein the absorbing structure has humidified from one minute in a 0.19% NaCl solution.

Another configuration can provide that the absorbing structure has a ratio of a shear strength of a sample with a width of 25 mm and a free clamping length of 200 mm from a wet to a dry condition in a range of 1-1.5 up to a ratio of 1-5.33, wherein the absorbing structure was humidified for 10 minutes in a 0.9% NaCl solution.

Furthermore it can also be provided that the layer structure in dry condition has a tear strength of 6.8-16 N/25 mm and in wet condition a tear strength of 3-6 N/25 mm.

There is also the option that the absorbing structure in a wet condition has a shear strength of 3 N/25 mm to 6 N/25 mm. In particular this range facilitates that flexibility is maintained for simultaneous integrity of the layer structure. According to one embodiment it can be provided that the absorbing structure in dry condition has a shear strength in a range between 5 and 7 N/25 mm. Another embodiment provides that the absorbing structure in dry condition has a shear strength of 11 and 17 N/25 mm.

Figure 9:
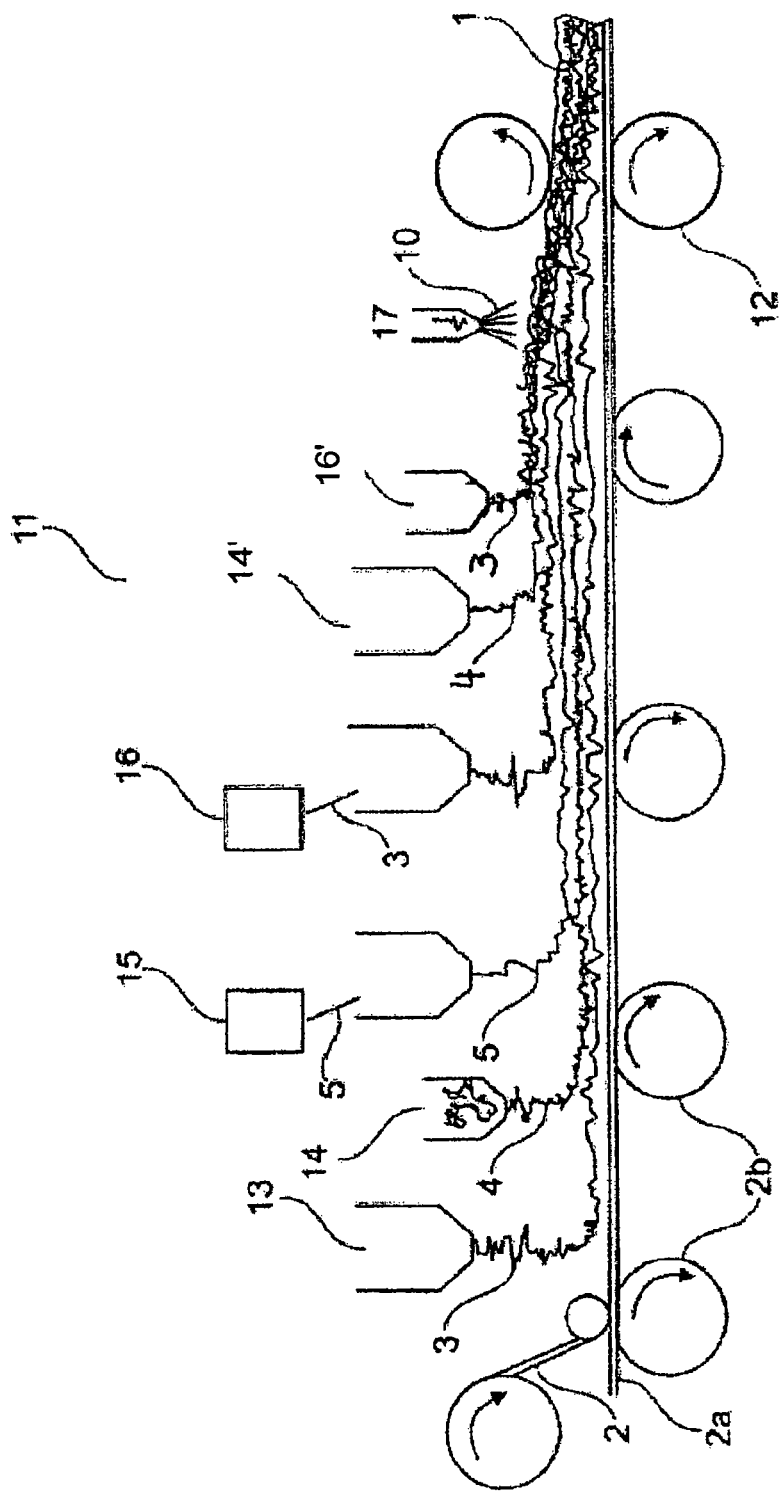
FIG. 9 illustrates a schematic view of an embodiment of a production device.

FIG. 9 illustrates a schematic representation of another possible configuration of a device 11 for producing an absorbing structure 1. An inline method is illustrated with a binding device for providing a carrier layer as a first layer made from an air laid material 2 which is applied to a screen band 2a with drive rollers 2b. Furthermore a first forming device 13 for depositing fluff pulp 3, a forming device 14 for providing an absorber, e.g. SAP particles 4, an additional forming device 15 for providing bonding fibers 5 is provided for forming a second layer 6 which is applied to the carrier layer 2. Fluff pulp 3 and absorber 4 are provided by the forming devices 16 and 14' in order to form a third layer 8 which is applied to the second layer 6. A forming device 16' for providing fluff pulp 3 and a device 17 for providing a bonding agent 10 are used to form a fourth layer 9 which is applied to the third layer. A bonding agent 10, e.g. a latex binder is applied through the device 17 onto the fourth layer 9, for example through application spraying or blade coating onto at least one outer surface of the layers. The layer structure can be heat activated after applying the binder material. This, however, can be performed through a heating device. The heating device preferably uses radiation heat. For example the heating device can be configured as a pass through station. Thus, or thereafter the layer structure is run through a device 12, for example a calendar which includes a calendar gap in which the layer structure is pressed together. The device 12 is for example a calendar with an arrangement of smooth running rollers but it can also be an infra red heater, an oven section or another heating element for activating the bonding fibers which glues the layers together with the bonding material but also with one another.

Based on the tests it has become apparent for example that a layer structure similar to the samples A and B has a distribution of layer portions with respect to the total weight of the layer structure which is as follows:

Layer 1 28-39% by weight
Layer 2 42-55% by weight
Layer 3 8.5-16.5% by weight

Thus, a tissue layer can be provided at least on one side, in particular as provided supra. Preferably a wet laid paper tissue is used. When a tissue layer is provided the tissue layer for example has a portion of the total weight of the layer structure in a range of preferably 2.7-5.5% by weight.

It is particularly preferred when none of the outer layers of the layer structures are bonded by embossing. Thus, it can be provided for example that a heat impact is provided which is applied evenly over the entire surface. Furthermore it is preferred according to one embodiment that only a dispersion binder is used for the outer layers, in particular using latex. Preferably a dispersion glue is used as described for samples A and B. Preferably a dispersion is used in which latex is used with a percentage of the dispersion preferably in a range between 11-19.5% by weight. Further preferably the dispersion glue, in particular the latex or EVA latex, is provided in dry condition of the layer structure, this means after evaporation of the liquid provided in the dispersion agent in a range between 1% by weight and 1.8% by weight respectively on each side of the layer structure.

Furthermore is has become apparent that also configurations are facilitated where one tissue layer is omitted and structural integrity of the respective outer layers is provided through the dispersion glue in combination with the fibers of the respective outer layer of the layer structure. In particular the wet tests have shown that integrity of the layer structure is also sufficiently provided with a configuration of this type.

In particular also the shear strength ranges described supra can be achieved with the proposed portions.

TABLE 1

Raw Materials and Composition of Sample A (VH460.103)

| | TRADE NAME | DESCRIPTION USE | CHEMICAL NAME | % BY WEIGHT | CAS REGISTRY # | COMPONENT SUPPLIER |
|---|---|---|---|---|---|---|
| 1 | GP 4881 or NB 416 | pulp, fibers | cellulose | 22 | 65996-61-4 | Georgia Pacific Weyerhaeuser |
| 2 | Biofluff TDR | pulp, fibers | cellulose | 21 | 65996-61-4 | Tembec Tartas |
| 3 | Favor Z 3269 | superabsorber | poly acrylic acid, partly neutralised | 45 | 9003-04-7 | Evonik |

TABLE 1-continued

Raw Materials and Composition of Sample A (VH460.103)

| | TRADE NAME | DESCRIPTION USE | CHEMICAL NAME | % BY WEIGHT | CAS REGISTRY # | COMPONENT SUPPLIER |
|---|---|---|---|---|---|---|
| 4 | Vinnapas 192 or Elite Ultra soft | polymer dispersion | ethylene vinyl acetate copolymer | 3 | 24937-78-8 | Wacker Polymers Celanese |
| 5 | T 255 | bicomponent fibers | polyethylene polyethylene terephthalate | 5 | 26221-73-8 25038-59-9 | Trevira |
| 6 | 3008 or KB 1800 | cellulose tissue | cellulose | 4 | 65996-61-4 | Cellu Tissue Swedish Tissue |
| 7 | | | | | | |
| 8 | | | | | | |
| 9 | | | | | | |
| 10 | | | | | | |

TABLE 2

Raw Materials and Composition of Sample B (VH600.101)

| | TRADE NAME | DESCRIPTION USE | CHEMICAL NAME | % BY WEIGHT | CAS REGISTRY # | COMPONENT SUPPLIER |
|---|---|---|---|---|---|---|
| 1 | GP 4881 or NB 416 | pulp, fibers | cellulose | 24 | 65996-61-4 | Georgia Pacific Weyerhaeuser |
| 2 | Biofluff TDR | pulp, fibers | cellulose | 20 | 65996-61-4 | Tembec Tartas |
| 3 | Favor Z 3269 | superabsorber | poly acrylic acid, partly neutralised | 45 | 9003-04-7 | Evonik |
| 4 | Vinnapas 192 or Elite Ultra soft | polymer dispersion | ethylene vinyl acetate copolymer | 3 | 24937-78-8 | Wacker Polymers Celanese |
| 5 | T 255 | bicomponent fibers | polyethylene polyethylene terephthalate | 5 | 26221-73-8 25038-59-9 | Trevira |
| 6 | 3008 or KB 1800 | cellulose tissue | cellulose | 3 | 65996-61-4 | Cellu Tissue Swedish Tissue |
| 7 | | | | | | |
| 8 | | | | | | |
| 9 | | | | | | |
| 10 | | | | | | |

TABLE 3

| Product Code | Position | GSM g/m² | Thickness 0.5 kPa dry mm | Thickness 0.5 kPa 10 g/g 0.9% NaCl Solution mm | Thickness 0.5 kPa free Absorption 1 min/2 min drip off mm |
|---|---|---|---|---|---|
| Measurement of Layer Thickness, Test Method WSP 120.6 | | | | | |
| VH600.101 | A4 | 631.01 | 7.55 | | |
| 7 cm × 7 cm sample | 1 | | 5.93 | 9.25 | |
| | 2 | | 6.10 | 8.16 | |
| | 3 | | 5.85 | 8.13 | |
| | 4 | | 6.12 | 8.46 | |
| | 5 | | 5.76 | 8.27 | |
| | 6 | | 5.75 | | 11 |
| | 7 | | 7.29 | | 11 |
| | 8 | | 7.45 | | 12 |
| | 9 | | 7.59 | | 12 |
| | 10 | | 7.69 | | 12 |
| | avg | | 6.55 | 8.45 | 11.6 |
| VH460.103 | A4 | 468.18 | 5.09 | | |
| 7 cm × 7 cm sample | 1 | | 5.06 | 6.20 | |
| | 2 | | 4.85 | 6.03 | |
| | 3 | | 4.93 | 5.80 | |
| | 4 | | 4.85 | 5.48 | |
| | 5 | | 4.90 | 5.64 | |
| | 6 | | 5.05 | | 9.79 |
| | 7 | | 5.13 | | 9.69 |
| | 8 | | 5.07 | | 9.81 |
| | 9 | | 5.14 | | 10.20 |
| | 10 | | 5.06 | | 10.18 |
| | avg | | 5.00 | 5.83 | 9.93 |

TABLE 3-continued

| Product Code | Position | GSM g/m² | Thickness 0.5 kPa dry mm | Thickness 0.5 kPa 10 g/g 0.9% NaCl Solution mm | Thickness 0.5 kPa free Absorption 1 min/2 min drip off mm |
|---|---|---|---|---|---|
| Measurement of Layer Thickness | | | | | |
| MT410.104 | A4 | 420.01 | 5.48 | | |
| 7 cm × 7 cm sample | 1 | | 5.30 | 5.61 | |
| | 2 | | 5.40 | 5.56 | |
| | 3 | | 5.28 | 5.55 | |
| | 4 | | 5.34 | 5.52 | |
| | 5 | | 5.47 | 5.54 | |
| | 6 | | 5.41 | | 7.00 |
| | 7 | | 5.50 | | 7.17 |
| | 8 | | 5.50 | | 6.97 |
| | 9 | | 5.43 | | 7.08 |
| | 10 | | 5.42 | | 7.20 |
| | avg | | 5.41 | 5.56 | 7.08 |
| VE500.200 | A4 | 473.84 | 1.59 | | |
| 7 cm × 7 cm sample | 1 | | 1.67 | 4.67 | |
| | 2 | | 1.64 | 4.38 | |
| | 3 | | 1.58 | 4.51 | |
| | 4 | | 1.58 | 3.66 | |
| | 5 | | 1.59 | 4.85 | |
| | 6 | | 1.60 | | 7.34 |
| | 7 | | 1.60 | | 7.24 |
| | 8 | | 1.56 | | 7.52 |
| | 9 | | 1.59 | | 6.93 |
| | 10 | | 1.55 | | 6.60 |
| | avg | | 1.60 | 4.41 | 7.13 |

TABLE 4

| Product Code | Position WSP-Method Unit | GSM g/m² | Bending Length cm | Stiffness* 90.5 mN*cm dry | Bending Length cm | Stiffness* 90.5 mN*cm wet | RF* 110.4 Opt. B N dry | 110.4 Opt. B wet | Bonding* 401 N dry | 401 wet |
|---|---|---|---|---|---|---|---|---|---|---|
| VH600.101 | 1 | 622.68 | 10.15 | 651.12 | 3.61 | 29.29 | 21.99 | 6.10 | 0.213 | 0.128 |
| | 2 | 646.35 | 10.13 | 671.89 | 3.65 | 31.43 | 25.40 | 6.57 | 0.142 | 0.148 |
| | 3 | 611.18 | 9.45 | 515.78 | 3.58 | 28.04 | 24.59 | 6.16 | 0.139 | 0.122 |
| | mean | 626.74 | | 612.93 | | 29.59 | 23.99 | 6.28 | 0.165 | 0.133 |
| VH460.103 | 1 | 477.34 | 8.58 | 301.50 | 2.99 | 12.76 | 23.69 | 4.37 | 0.143 | 0.145 |
| | 2 | 477.18 | 7.98 | 242.49 | 2.79 | 10.36 | 23.45 | 4.00 | 0.109 | 0.109 |
| | 3 | 491.84 | 8.13 | 264.30 | 2.94 | 12.50 | 22.13 | 4.70 | 0.114 | 0.114 |
| | mean | 482.12 | | 269.43 | | 11.87 | 23.09 | 4.36 | 0.122 | 0.123 |
| MT410.104 | 1 | 432.84 | 11.68 | 689.69 | 3.55 | 19.36 | 20.92 | 8.54 | 0.799 | 0.344 |
| | 2 | 424.18 | 11.58 | 658.68 | 3.31 | 15.38 | 17.35 | 8.14 | 0.565 | 0.342 |
| | 3 | 446.68 | 11.53 | 684.67 | 3.39 | 17.40 | 23.15 | 9.85 | 0.426 | 0.453 |
| | mean | 434.57 | | 677.68 | | 17.38 | 20.47 | 8.84 | 0.597 | 0.38 |
| VE500.200 | 1 | 484.01 | 7.15 | 176.92 | 2.91 | 11.93 | 13.54 | 2.82 | 0.460 | 0.034 |
| | 2 | 452.84 | 6.49 | 123.79 | 2.98 | 11.98 | 10.48 | 2.36 | 0.553 | 0.056 |
| | 3 | 436.01 | 6.86 | 140.76 | 2.96 | 11.31 | 11.60 | 2.48 | 0.486 | 0.077 |
| | mean | 457.62 | | 147.15 | | 11.74 | 11.87 | 2.55 | 0.5 | 0.056 |

*narrow strip (1 inch = 25 mm)
RF = Tear Strength, 200 mm Clamping Distance, Velocity 100 mm/min

| | wet | (10 g/g 0.9% NaCl) | for VH600.101 40 ml other products 30 ml |
|---|---|---|---|
| Absorption in g/g WSP 10.1 | | 0.9% NaCl solution 1 min. submersion 2 min. hanging | |

| Product Code | Position 1 | 2 | 3 | 4 | 5 | mean g/g | Method Concert 10 min. submersion/ 10 sec. dry | ABS/Total* g/g |
|---|---|---|---|---|---|---|---|---|
| VH600.101 | 17.75 | 17.35 | 17.36 | 18.06 | 17.63 | 17.63 | 25.98 | 30.12 |
| VH460.103 | 17.23 | 18.11 | 17.29 | 17.51 | 17.74 | 17.58 | 27.20 | 33.68 |

TABLE 4-continued

| | | | | | | | | |
|---|---|---|---|---|---|---|---|---|
| MT410.104 | 15.44 | 14.97 | 15.75 | 15.33 | 14.83 | 15.26 | 18.75 | 20.77 |
| VE500.200 | 12.37 | 12.97 | 12.68 | 12.98 | 11.37 | 12.47 | 18.94 | 24.47 |

*tea bag test

| Tear Strength | | in N/25 mm |
|---|---|---|
| VH600.101 | complete | 16.93 |
| | | 19.87 |
| | | 16.69 |
| VH600.101 | tissue | 15.02 |
| | | 14.89 |
| | | 13.65 |
| VH600.101 | upper side | 5.05 |
| | | 5.63 |
| | | 4.71 |
| | | 4.64 |

The invention claimed is:

1. An absorbing structure with a sequence of layers, comprising:
    at least a first and a second outer surface and at least one internal liquid storage layer disposed there between;
    a first liquid storage layer comprising fluff pulp, bonding fibers and super absorbing polymer (SAP); and
    a second liquid storage layer comprising fluff pulp and super absorbing polymer (SAP);
    wherein the layers are disposed on top of one another and form a ply structure,
    wherein the at least one internal liquid storage layer includes a cellulose material, a super absorbing polymer (SAP), and
    less binder material than the first and a second liquid storing layer of the absorbing structure, the at least one internal liquid storage layer being disposed between and in direct contact with the first and second liquid storing layers, and,
    wherein at least one of the first and second outer surfaces comprises a latex based binder.

2. The absorbing structure according to claim 1, comprising at last three plies,
    wherein a center ply includes less binder material than the other two plies.

3. The absorbing structure according to claim 2, wherein at least a substantial portion of the ply with less binder material comprises treated and/or non treated cellulose material.

4. The absorbing structure according to claim 3, wherein the SAP in the internal layer comprises SAP particles and/or SAP fibers which are disposed moveable relative to one another in the internal liquid storage layer when liquid is absorbed and/or pressure is introduced.

5. The absorbing structure according to claim 1, wherein the first and second outer surfaces comprise latex based binder material.

6. The absorbing structure according to claim 5, comprising a paper tissue ply as a first ply, a second ply with fluff pulp, bonding fibers and super absorber, a third ply with fluff pulp and with super absorber, and a fourth ply with fluff pulp and bonding fibers, wherein the third ply comprises less bonding fibers than the respective second ply and the fourth ply.

7. The absorbing structure according to claim 6, wherein the third ply facilitates a relative moveability between the second ply and the fourth ply in a longitudinal direction of the absorbing structure when wet.

8. The absorbing structure according to claim 6, wherein the third ply does not comprise binder material.

9. The absorbing structure according to claim 1, wherein the absorbing structure has a ratio of a shear strength of a sample with a width of 25 mm and with a free clamping length of 200 mm from a wet condition to a dry condition in a range of 1 to 1.2 to 1 to 4 when humidified for one minute in a 0.9% NaCl solution.

10. The absorbing structure according to claim 1, wherein the absorbing structure has a ratio of a shear strength of a sample with a width of 25 mm and with a free clamping length of 200 mm from a wet condition to a dry condition in a range of 1 to 1.5 to 1 to 5.33 when humidified for one minute in a 0.9% NaCl solution.

11. The absorbing structure according to claim 1, wherein the layer structure in dry condition has a tear strength of 6.8 to 16 N/25 mm and in wet condition has a tear strength of 3 to 6 N/25 mm.

12. The absorbing structure according to claim 1, wherein the absorbing structure has a shear strength of 3 N/25 mm to 6 N/25 mm in a wet condition.

13. An absorbing structure according to claim 1 in the form of a disposable hygiene product.

14. The absorbing structure according to claim 1, wherein the at least one internal liquid storage layer does not comprise binder material.

15. The absorbing structure according to claim 1, wherein the SAP comprises SAP particles and/or SAP fibers capable of sliding on each other when wet.

16. The absorbing structure according to claim 1, wherein the cellulose material comprises cellulose fibers.

17. A method for producing an absorbing structure, comprising at least the following steps:
    laying fluff pulp, SAP and a binder material as a second ply on a support layer;
    laying fluff pulp and SAP on the second ply as a third ply;
    laying a fourth ply made of fluff pulp and binder material on the third ply;
    applying a latex based binder material on at least one outer surface of the plies such that the third ply includes less binder material than the second ply and fourth ply adjacent to the third ply;
    supplying the plies to a calender which includes a calender gap; and
    compressing the plies in the calender gap.

18. A device for producing an absorbing structure, comprising at least:
    a sifting band for laying plies for forming a ply structure;
    a first forming device through which at least cellulose fibers, super absorbing polymer (SAP) and a binder material are applicable to the sifting band;
    a second forming device, through which cellulose fibers and SAP are applicable to the sifting band for forming an additional ply;

a third forming device, through which a binder material and cellulose fibers are applicable to the sifting band as an additional ply;

at least one application station through which a latex based binder material is applicable at least on an outer surface of the ply structure;

a compressing station, through which the ply structure layer is compressible, and wherein a feeding of binder material to the second forming device is adjusted such that less binder material is supplied than in the first and third forming device.

19. The device for producing an absorbing structure according to claim 18, wherein the compressing station comprises a calender.

* * * * *